United States Patent
Alam

(10) Patent No.: US 11,970,473 B2
(45) Date of Patent: Apr. 30, 2024

(54) NOOTKATONE DERIVATIVES AND METHODS OF USING THE SAME

(71) Applicant: Arkansas State University—Jonesboro, State University, AR (US)

(72) Inventor: Mohammad Abrar Alam, Jonesboro, AR (US)

(73) Assignee: Arkansas State University—Jonesboro, State University, AR (US)

( * ) Notice: Subject to any disclaimer, the term of this patent is extended or adjusted under 35 U.S.C. 154(b) by 0 days.

(21) Appl. No.: 17/710,485

(22) Filed: Mar. 31, 2022

(65) Prior Publication Data

US 2022/0324823 A1    Oct. 13, 2022

Related U.S. Application Data

(60) Provisional application No. 63/168,883, filed on Mar. 31, 2021.

(51) Int. Cl.
| | |
|---|---|
| *C07D 277/84* | (2006.01) |
| *A61K 31/428* | (2006.01) |
| *A61P 31/04* | (2006.01) |
| *C07D 417/04* | (2006.01) |
| *C07D 417/06* | (2006.01) |
| *C07D 417/10* | (2006.01) |
| *C07D 417/12* | (2006.01) |

(52) U.S. Cl.
CPC ............ *C07D 277/84* (2013.01); *A61P 31/04* (2018.01); *C07D 417/04* (2013.01); *C07D 417/06* (2013.01); *C07D 417/10* (2013.01); *C07D 417/12* (2013.01)

(58) Field of Classification Search
CPC .. C07D 277/84; C07D 417/04; C07D 417/06; C07D 417/10; C07D 417/12; A61P 31/04; A61K 31/428
See application file for complete search history.

(56) References Cited

U.S. PATENT DOCUMENTS

| 10,596,153 B2 | 3/2020 | Alam |
| 2021/0317160 A1 | 10/2021 | Alam |

FOREIGN PATENT DOCUMENTS

| WO | 2020018997 | 1/2020 |

OTHER PUBLICATIONS

Alam, M.A.; Alsharif, Z.; Alkhattabi, H.; Jones, D.; Delancey, E.; Gottsponer, A.; Yang, T. Hexafluoroisopropyl alcohol mediated synthesis of 2,3-dihydro-4H-pyrido[1,2-a]pyrimidin-4-ones. Sci. Rep. 2016, 6, 36316.

Ali, M.A., et al. "Benign synthesis of thiazolo-androstenone derivatives as potent anticancer agents." OrIDFnic letters 20.18 (2018): 5927-5932.

Alkhaibari, I.S. et al. Synthesis of Chimeric Thiazolo-Nootkatone Derivatives as Potent Antimicrobial Agents. ChemMedChem. Sep. 6, 2021;16(17):2628-2637. doi: 10.1002/cmdc.202100230. Epub Jun. 9, 2021.

Allison, D. et al. Synthesis and antimicrobial studies of novel derivatives of 4-(4-formyl-3-phenyl-1Hpyrazol-1-yl) benzoic acid as potent anti-Acinetobacter baumannii agents. Bioorg. Med. Chem. Lett. 2017, 27, 387-392.

Alnufaie, R. et al. Design and synthesis of 4-[4-formyl-3-(2-naphthyl)pyrazol-1-yl]benzoic acid derivatives as potent growth inhibitors of drug-resistant *Staphylococcus aureus*. The Journal of Antibiotics 2020, 73 (12), 818-827.

Alnufaie, R. et al. Synthesis and Antimicrobial Studies of Coumarin-Substituted Pyrazole Derivatives as Potent Anti-*Staphylococcus aureus* Agents. Molecules 2020, 25 (12), 2758.

Alptüzün, V. et al. Synthesis and antimicrobial activity of some pyridinium salts. Molecules (Basel, Switzerland) 2009, 14 (12), 5203-5215.

Alsharif, Z.A. & Alam, M.A. Modular synthesis of thiazoline and thiazole derivatives by using a cascade protocol. RSC Advances 2017, 7, 32647-32651.

Alsharif, Z.A. et al. Hexafluoroisopropanol mediated benign synthesis of 2H-pyrido[1,2-a]pyrimidin-2-ones by using a domino protocol. New J. Chem. 2017, 41, 14862-14870.

Ayati, A. et al. Recent applications of 1,3-thiazole core structure in the identification of new lead compounds and drug discovery. Eur. J. Med. Chem. 2015, 97, 699-718.

Balasubramanian, S. et al. A New Bioactive Compound From the Marine Sponge-Derived *Streptomyces* sp. SBT348 Inhibits Staphylococcal Growth and Biofilm Formation. Front Microbiol 2018, 9, 1473.

Berditsch, M et al. Supreme activity of gramicidin S alDFinst resistant, persistent and biofilm cells of staphylococci and enterococci. Scientific Reports 2019, 9 (1), 17938.

Boucher, H. W. et al. Bad bugs, no drugs: no ESKAPE! An update from the Infectious Diseases Society of America. Clin Infect Dis 2009, 48 (1), 1-12.

Brinkman, C. L. et al. Exposure of Bacterial Biofilms to Electrical Current Leads to Cell Death Mediated in Part by Reactive Oxygen Species. PLoS One 2016, 11 (12), e0168595.

CDC About Antibiotic Resistance. https://www.cdc.gov/drugresistance/about.html (accessed Oct. 30, 2020).

CDC Antibiotic / Antimicrobial Resistance (AR / AMR). https://www.cdc.gov/drugresistance/biggest_threats.html (accessed Sep. 17, 2019).

CDC Methicillin-resistant *Staphylococcus aureus* (MRSA). https://www.cdc.gov/mrsa/index.html (accessed Oct. 30, 2020).

CDC Vancomycin-Resistant Enterococci (VRE). https://www.cdc.gov/drugresistance/pdf/threats-report/vre-508.pdf (accessed May 23, 2020).

Chhabria, M. T. et al. A Review on Chemistry, Synthesis and Therapeutic Importance of its Derivatives. Curr. Top. Med. Chem. (Sharjah, United Arab Emirates) 2016, 16 (26), 2841-2862.

(Continued)

*Primary Examiner* — Bruck Kifle
(74) *Attorney, Agent, or Firm* — Quarles & Brady, LLP

(57) ABSTRACT

Nootkatone derivatives comprising a fused thiazole ring and methods of using the same are disclosed herein.

20 Claims, 14 Drawing Sheets

(56) References Cited

OTHER PUBLICATIONS

Delancey, E. et al. Synthesis of 4,4'-(4-Formyl-1H-pyrazole-1,3-diyl)dibenzoic Acid Derivatives as Narrow Spectrum Antibiotics for the Potential Treatment of Acinetobacter Baumannii Infections. Antibiotics 2020, 9 (10), 650.
FDA Nootkatone Now Registered by EPA. https://www.epa.gov/pesticides/nootkatone-now-registered-epa (accessed Oct. 30, 2020).
Farha, M.A. et al. Inhibition of WTA synthesis blocks the cooperative action of PBPs and sensitizes MRSA to beta-lactams. ACS Chem Biol 2013, 8 (1), 226-33.
Ghosh, A. et al. Small-Molecule Inhibition of Bacterial Biofilm. ACS OmeIDF 2020, 5 (7), 3108-3115.
Guo, Y. Non-food bioactive natural forest products as insecticide candidates: Preparation, biological evaluation and molecular docking studies of novel N-(1,3-thiazol-2-yl)carboxamides fused (+)-nootkatone from Chamaecyparis nootkatensis [D. Don] Spach. Industrial Crops and Products 2020, 156, 112864.
Hu, X. et al. Triazole-Linked Glycolipids Enhance the Susceptibility of MRSA to beta-Lactam Antibiotics. ACS Med Chem Lett 2015, 6 (7), 793-7.
Kim, W. et al. Discovery and Optimization of nTZDpa as an Antibiotic Effective AIDFinst Bacterial Persisters. ACS Infectious Diseases 2018, 4 (11), 1540-1545.
Kumar, L. Matrix metalloprotease-1 inhibits and disrupts Enterococcus faecalis biofilms. PLoS One 2019, 14 (1), e0210218.
Lam, A.K. et al. Low-Molecular-Weight Branched Polyethylenimine Potentiates Ampicillin alDFinst MRSA Biofilms. ACS Medicinal Chemistry Letters 2020, 11 (4), 473-478.
Li, C. et al. Antimicrobial activities of amine- and guanidine-functionalized cholic acid derivatives. Antimicrob. Agents Chemother. 1999, 43 (6), 1347-1349.
Meeker, D.G. et al. Evaluation of Antibiotics Active alDFinst Methicillin-Resistant *Staphylococcus aureus* Based on Activity in an Established Biofilm. Antimicrob. Agents Chemother. 2016, 60 (10), 5688-94.
Mistry, T. L.; Truong, L.; Ghosh, A. K.; Johnson, M. E.; Mehboob, S., Benzimidazole-Based FabI Inhibitors: A Promising Novel Scaffold for Anti-staphylococcal Drug Development. ACS Infectious Diseases 2017, 3 (1), 54-61.
Moisse, K. Antibiotic Resistance Could Bring 'End of Modern Medicine'. http://abcnews.go.com/blogs/health/2012/03/16/antibiotic-resistance-could-bring-end-of-modern-medicine/ (accessed May 1, 2020).
Murase, T. Nootkatone, a characteristic constituent of grapefruit, stimulates energy metabolism and prevents diet-induced obesity by activating AMPK. American journal of physiology. Endocrinology and metabolism 2010, 299 (2), E266-75.
Nguyen, T. H. et al. Host Response to *Staphylococcus epidermidis* Colonization and Infections. Frontiers in cellular and infection microbiology 2017, 7, 90.
Okolo, C. et al. "Hexafluoroisopropanol-mediated domino reaction for the synthesis of thiazolo-androstenones: potent anticancer agents." ACS omeIDF 3.12 (2018): 17991-18001.

Palomo, S. Sponge-Derived Kocuria and *Micrococcus* spp. as Sources of the New Thiazolyl Peptide Antibiotic Kocurin. Mar Drugs 2013, 11 (4), 1071-1086.
Perlmutter, S.J. et al. Hergenrother, P. J., Compound Uptake into *E. coli* can be Facilitated by N-Alkyl Guanidiniums and Pyridiniums. ACS Infectious Diseases 2021, 7 (1), 162-173.
Raafat, D. et al. Fighting *Staphylococcus aureus* Biofilms with Monoclonal Antibodies. Trends in Microbiology 2019, 27 (4), 303-322.
Richter, M. F. et al. Predictive compound accumulation rules yield a broad-spectrum antibiotic. Nature 2017, 545 (7654), 299-304.
Roy, R. et al. Strategies for combating bacterial biofilms: A focus on anti-biofilm agents and their mechanisms of action. Virulence 2018, 9 (1), 522-554.
Saini, H. et al. Azithromycin-Ciprofloxacin-Impregnated Urinary Catheters Avert Bacterial Colonization, Biofilm Formation, and Inflammation in a Murine Model of Foreign-Body-Associated Urinary Tract Infections Caused by Pseudomonas aeruginosa. Antimicrobial agents and chemotherapy 2017, 61 (3), e01906-16.
Sauer, A.M. et al. An Efficient and Economic Asymmetric Synthesis of (+)-Nootkatone, Tetrahydronootkatone, and Derivatives. Org. Lett. 2009, 11 (16), 3530-3533.
Song, S. et al. Combatting Persister Cells With Substituted Indoles. Front Microbiol 2020, 11, 1565.
Spellberg, B. et al. Infectious Diseases Society of, A., The epidemic of antibiotic-resistant infections: a call to action for the medical community from the Infectious Diseases Society of America. Clin Infect Dis 2008, 46 (2), 155-64.
Tal-Jasper, R.; Katz, D. E.; Amrami, N.; Ravid, D.; Avivi, D.; Zaidenstein, R.; Lazarovitch, T.; Dadon, M.; Kaye, K. S.; Marchaim, D., Clinical and Epidemiological Significance of Carbapenem Resistance in Acinetobacter baumannii Infections. Antimicrob. Agents Chemother. 2016, 60 (5), 3127-3131.
Wang, Y. Thiazole Amides, A Novel Class of AllDFecides alDFinst Freshwater Harmful AllDFe. Scientific reports 2018, 8 (1), 8555.
Whitt, J. et al. J et al. Synthesis and Antimicrobial Studies of 4-[3-(3-Fluorophenyl)-4-formyl-1H-pyrazol-1-yl]benzoic Acid and 4-[3-(4-Fluorophenyl)-4-formyl-1H-pyrazol-1-yl]benzoic Acid as Potent Growth Inhibitors of Drug-Resistant Bacteria. ACS OmeIDF 2019, 4 (10), 14284-14293.
Whitt, J. et al. Synthesis of Hydrazone Derivatives of 4-[4-Formyl-3-(2-oxochromen-3-yl)pyrazol-1-yl]benzoic acid as Potent Growth Inhibitors of Antibiotic-resistant *Staphylococcus aureus* and Acinetobacter baumannii. Molecules 2019, 24 (11), 2051.
Worthington, R. J. et al. Small molecule control of bacterial biofilms. OrIDFnic & Biomolecular Chemistry 2012, 10 (37), 7457-7474.
Zakeyha, A.A. et al. Synthesis and antimicrobial studies of hydrazone derivatives of 4-[3-(2,4-difluorophenyl)-4-formyl-1Hpyrazol-1-yl]benzoic acid and 4-[3-(3,4-difluorophenyl)-4-formyl-1Hpyrazol-1-yl]benzoic acid. Bioorg. Med. Chem. Lett. 2018, 28, 2914-2919.
Zhang, K. Promising Therapeutic Strategies AIDFinst Microbial Biofilm Challenges. Frontiers in Cellular and Infection Microbiology 2020, 10 (359).
Sharma, P.C. et al. Thiazole-containing compounds as therapeutic targets for cancer therapy. 2020.Eur J Med Chem. 188:112016.

R = alkyl and substituted alkyl derivatives

NOOTKATONE DERIVATIVES AND METHODS OF USING THE SAME

CROSS-REFERENCE TO RELATED APPLICATIONS

The present application claims priority to U.S. Provisional Patent Application No. 63/168,883, filed Mar. 31, 2021, the entire contents of which are hereby incorporated by reference.

FIELD OF THE INVENTION

The disclosed technology is generally directed to antimicrobial compounds. More particularly the technology is directed to nootkatone derivatives for antimicrobial applications.

BACKGROUND OF THE INVENTION

Antibiotic resistance is one of the world's urgent public health problems, which affects people at any stage of life, healthcare system, veterinary and agricultural industries. More than 2.8 million people are infected with antibiotic-resistance bacteria or fungi and more than 35,000 people die of these infections in the United States alone. Many modern healthcare advances such as joint replacements, organ transplants, cancer therapy, and the treatment of chronic diseases like diabetes, arthritis, and asthma are dependent on the ability to fight infections using antibiotics.[12] *Staphylococcus aureus* is found in about 30% people's nares. This bacterium can cause sepsis, pneumonia, endocarditis, and osteomyelitis. The treatment of *S. aureus* infections often becomes challenging due to its ability to develop resistance against approved antibiotics. Based on *S. aureus* sensitivity to antibiotics, this bacterium is known as different germs including: methicillin-sensitive *S. aureus* (MSSA), methicillin-resistant *S. aureus* (MRSA), vancomycin-intermediate *S. aureus* (VISA), and vancomycin-resistant *S. aureus* (VRSA). Penicillin and daptomycin resistant *S. aureus* have also been reported over the years. Although MRSA is most common drug-resistant *S. aureus* strain, any strain of this bacterium could be dangerous.[12-13] As a result, there is a need for new antimicrobial compounds and compositions.

BRIEF SUMMARY OF THE INVENTION

Nootkatone derivatives comprising a fused thiazole ring and methods of using the same are disclosed herein. One aspect of the technology provides for compounds of formula

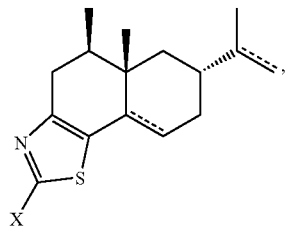

or a pharmaceutically acceptable salt thereof, wherein ---- represents a saturated or an unsaturated bond and X is selected from a substituted or an unsubstituted aryl, a substituted or an unsubstituted alkyl, a substituted or an unsubstituted heterocycle, $-NR^1R^2$ wherein $R^1$ and $R^2$ are independently selected from hydrogen, a substituted or an unsubstituted aryl, a substituted or an unsubstituted alkyl, or $R^1$ and $R^2$ together form a substituted or an unsubstituted heterocycle. In some embodiments, ---- is the unsaturated bond. In other embodiments, ---- is the saturated bond.

In some embodiments X is the substituted or the unsubstituted aryl. In particular embodiments, X is the substituted aryl. Suitably, X is

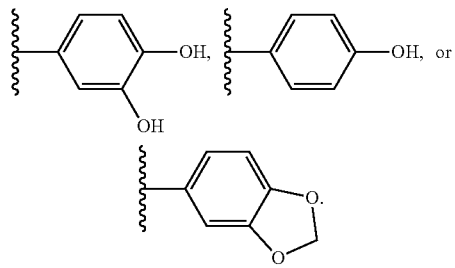

In some embodiments, X is the unsubstituted aryl.

In some embodiments, X is the substituted or the unsubstituted alkyl.

In some embodiments, X is the substituted or the unsubstituted heterocycle.

In some embodiments, X is $-NR^1R^2$.

In some embodiments, ---- is an unsaturated bond and X is selected from

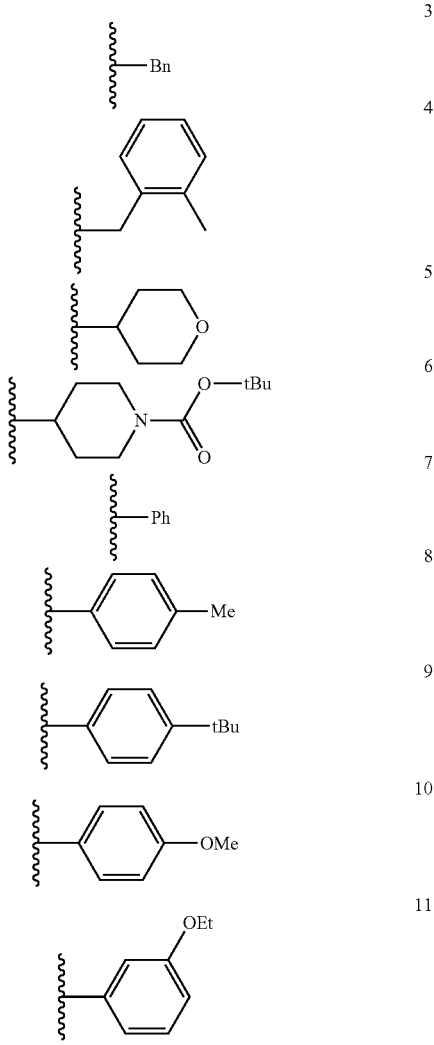

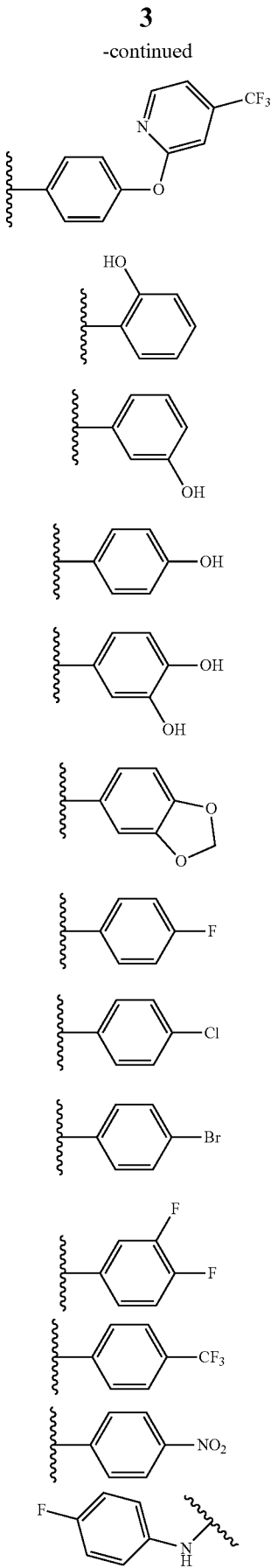
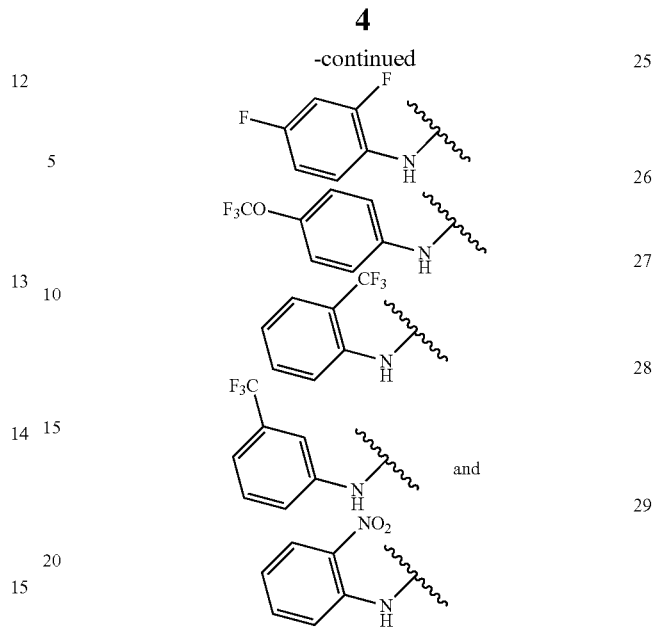

Another aspect provides for pharmaceutical compositions comprising an effective amount of any of the compounds disclosed herein and a pharmaceutically acceptable excipient, carrier, or diluent.

Another aspect provides for is a method for the treatment of a subject in need of a treatment for an infection by a microbe. The method may comprise administering an effective amount of any of the compounds described herein or a pharmaceutical composition comprising the effective amount of the compound to the subject. In some embodiments, the microbe is antimicrobial resistant. In some embodiments, the microbe is a persister. In some embodiments, the microbe is a Gram-positive bacterium. Exemplary Gram-positive bacterium includes, without limitation, S. aureus, a S. epidermidis, B. subtilis, or E. faecium. In some embodiments, the Gram-positive bacterium is a methicillin-resistant S. aureus. In some embodiments, the microbe is a Gram-negative bacterium. Exemplary Gram-negative bacterium includes, without limitation, A. baumannii.

Another aspect provided for is a method for inhibiting growth or proliferation or killing a microbe. The method may comprise contacting the microbe with an effective amount of any of the compounds described herein. In some embodiments, the microbe is antimicrobial resistant. In some embodiments, the microbe is a persister. In some embodiments, the microbe is a Gram-positive bacterium. Exemplary Gram-positive bacterium includes, without limitation, S. aureus, a S. epidermidis, B. subtilis, or E. faecium. In some embodiments, the Gram-positive bacterium is a methicillin-resistant S. aureus. In some embodiments, the microbe is a Gram-negative bacterium. Exemplary Gram-negative bacterium includes, without limitation, A. baumannii.

These and other aspects of the technology will be further described herein.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

Disclosed herein a nootkatone derivatives and methods of using the same. The compounds disclosed herein comprise fused-thiazole derivatives of nootkatone. As demonstrated in the Examples, the presently disclosed compounds are effective antimicrobials for killing or inhibiting the growth or proliferation of microbes, such as Gram-positive and Gram-negative bacteria. A notable advantage of the compounds disclosed herein is that they effective against antimicrobial-resistant and persister strains. The compounds also demonstrated greater potency than front-line antibiotics, such as vancomycin and gentamicin, and are non-toxic in human cell lines.

Compounds

Figure 1:
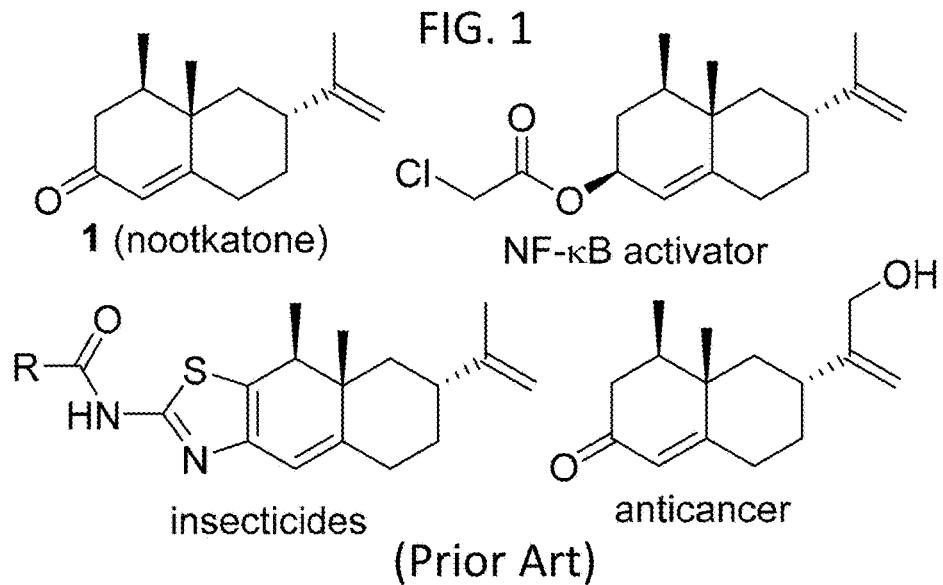
FIG. 1 illustrates Nootkatone (1) and prior art derivatives.

The compounds disclosed herein comprise fused-thiazole derivatives of nootkatone. Nootkatone (1) is an enone containing sesquiterpenoid natural product found in grapefruits and several other organisms (FIG. 1).[2] Nootkatone has been known for several decades and several groups have reported the total synthesis of this bioactive molecule.[20-23] This small molecule is effective insect repellent or insecticide and it has been approved by Environmental Protection Agency (EPA) to control mosquito-borne diseases including dengue and Zika.[3] Nootkatone is known to show potent inhibition effect on collagen-, thrombin-, and AA-induced platelet aggregation,[4] AMP activated protein kinase (AMPK) activation,[5] anti-inflammatory, neuroprotective effect,[6] and NF-κB activation properties.[7] Fused thiazole derivatives have also been shown to possess insecticidal activity.[8]

The compounds disclosed herein have the formula

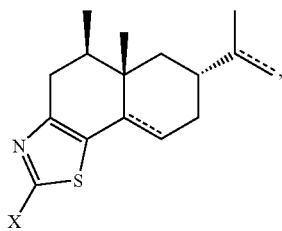

wherein ==== represents a saturated or an unsaturated bond and X is selected from a substituted or unsubstituted aryl, a substituted or unsubstituted alkyl, a substituted or unsubstituted heterocycle, —NR$^1$R$^2$ wherein R$^1$ and R$^2$ are independently selected from hydrogen, a substituted or an unsubstituted aryl, a substituted or unsubstituted alkyl, or R$^1$ and R$^2$ together form a substituted or an unsubstituted heterocycle.

In some embodiments, ==== is an unsaturated bond. In other embodiments, ==== is a saturated bond.

In some embodiments, X is a substituted aryl. In other embodiments, X is an unsubstituted aryl. In particular embodiments, the aryl is phenyl. When the aryl is substituted, the aryl may comprise one or more substituents. Exemplary substituents include, without limitation, hydroxyl; a substituted or unsubstituted alkyl, e.g., Me, tBu, or —CF$_3$; a substituted or unsubstituted alkoxyl, e.g., OMe, OEt, OCF$_3$; halo, e.g., Cl or F; nitro; cyano; —C(O)OR, where R is hydrogen or an alkyl; —NHC(O)R, where R is an alkyl; or any combination thereof. In some embodiments, X is

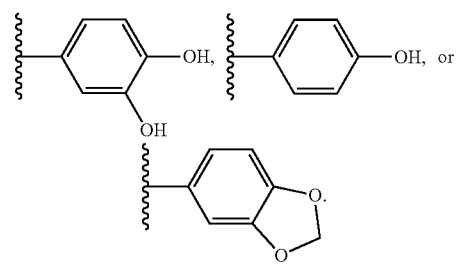

In some embodiments, X is a substituted alkyl. In other embodiments, X is an unsubstituted alkyl. The alkyl may be branched or unbranched. In some embodiment, the alkyl is a $C_1$-$C_6$ alkyl. Exemplary alkyl groups include, without limitation, methyl, ethyl, isopropyl, n-propyl, 2-methylpropyl, n-butyl, n-pentyl, and the like. Exemplary substituents include halo substituents, e.g., —CF$_3$, or a heterocycle, e.g., morpholinyl, aryl substituents that may be optionally substituted, e.g., optionally substituted phenyl.

In some embodiments, X is a substituted heterocycle. In other embodiments, an unsubstituted heterocycle. Exemplary heterocycles include, without limitation, piperidinyl, morpholinyl, or tetrahydropyranyl. Exemplary substituents include alkyl substituents —C(=O)OR, where R is an alkyl, e.g., methyl of tBu.

In some embodiments, X is —NR$^1$R$^2$ and R$^1$ and R$^2$ are independently selected from hydrogen, a substituted or an unsubstituted aryl, a substituted or unsubstituted alkyl, or R$^1$ and R$^2$ together form a substituted or an unsubstituted heterocycle. In some embodiments, one of R$^1$ and R$^2$ is hydrogen and the other is a substituted or an unsubstituted aryl or a substituted or unsubstituted alkyl. In some embodiments, both R$^1$ and R$^2$ are hydrogen. In other embodiments, neither R$^1$ nor R$^2$ are hydrogen. In some embodiments, R$^1$ and R$^2$ together form a substituted or an unsubstituted heterocycle.

The compounds disclosed herein were prepared by reacting epoxy nootkatone with thiazole and thioamide derivatives in acetic acid as illustrated in Scheme 1. The intended products were synthesized in very good yield and excellent purity for biological testing.

Scheme 1 Synthesis of fused-thiazole derivative with nootkatone.

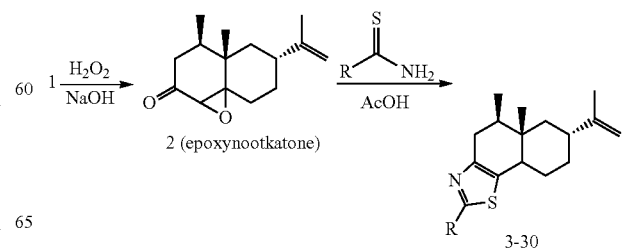

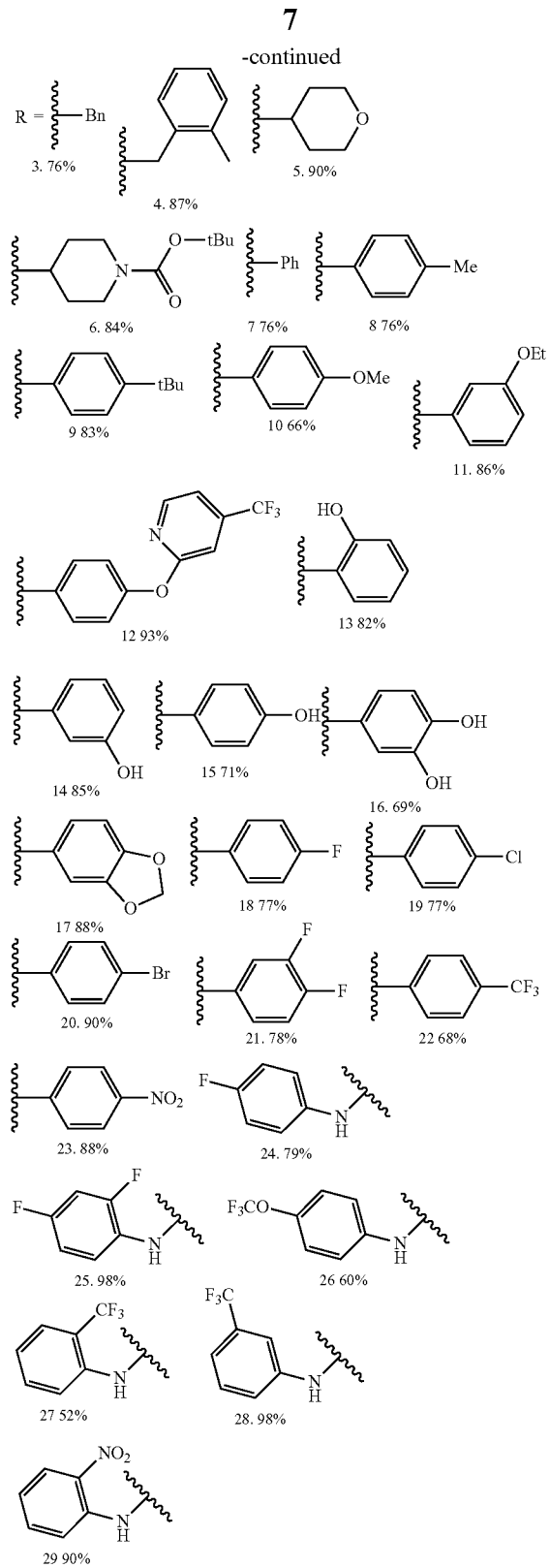

Additional schemes and exemplary compounds according to the present technology are provided in FIGS. 5-12.

As used herein, an asterick "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, 1-6, or 1-4 carbon atoms, referred to herein as $C_1$-$C_{12}$ alkyl, $C_1$-$C_{10}$-alkyl, $C_1$-$C_6$-alkyl, $C_1$-$C_4$-alkyl respectively.

The term "alkylene" refers to a diradical of an alkyl group. An exemplary alkylene group is —$CH_2CH_2$—.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxyl" group The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$-alkenyl, $C_2$-$C_{10}$-alkenyl, and $C_2$-$C_6$-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as $C_2$-$C_{12}$-alkynyl, $C_2$-$C_{10}$-alkynyl, and $C_2$-$C_6$-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of an cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a $C_5$-$C_{14}$, $C_5$-$C_{12}$, $C_5$-$C_8$, or $C_5$-$C_6$ membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system.

Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using Cx-Cx nomenclature where x is an integer specifying the number of ring atoms. For example, a $C_3$-$C_7$ heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

An "epoxide" is a cyclic ether with a three-atom ring typically include two carbon atoms and whose shape approximates an isosceles triangle. Epoxides can be formed by oxidation of a double bound where the carbon atoms of the double bond form an epoxide with an oxygen atom.

The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$ are independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereo isomers of these compounds and mixtures thereof. Stereoisomers include enantiomers and diastereomers. Mixtures of enantiomers or diastereomers may be designated "(f)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.)

Pharmaceutical Compositions

The compounds disclosed herein may be formulated as pharmaceutical compositions that include: an effective amount of one or more compounds and one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 µM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents.

Suitable diluents may include pharmaceutically acceptable inert fillers.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form, which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures. The compounds for use according to the methods of disclosed herein may be administered as a single compound or a combination of compounds.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Pharmaceutically acceptable esters and amides of the compounds can also be employed in the compositions and methods disclosed herein.

In addition, the methods disclosed herein may be practiced using solvate forms of the compounds or salts, esters, and/or amides, thereof. Solvate forms may include ethanol solvates, hydrates, and the like.

Methods

Methods for treating subjects with the compounds disclosed herein are provided. Suitably the method for treating a subject comprises administering to the subject an effective amount of one or more of the compounds disclosed herein or a pharmaceutical composition comprising the effective amount of one or more of the compounds disclosed herein. As used herein, a "subject" may be interchangeable with "patient" or "individual" and means an animal, which may be a human or non-human animal, in need of treatment. A "subject in need of treatment" may include a subject having a disease, disorder, or condition that is responsive to therapy with one or more of the compounds disclosed herein. In some embodiments, the subject is responsive to therapy with one or more of the compounds disclosed herein in combination with one or more additional therapeutic agents. For example, a "subject in need of treatment" may include a subject in need of treatment for a microbial infection. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

In some embodiments, the subject has a microbial infection and may show symptoms associated therewith. Symptoms associated with microbial infections can be varied depending on the location and severity of the infection. In some instances the infection is located in or on the skin or an inner organ, tissue, or fluids, such as lungs, heart, blood, bone, joints, or gastrointestinal tract. *S. aureus* infection, for example, may be associated with sepsis, pneumonia, endocarditis, osteomyelitis, skin infections, food poisoning, toxic shock syndrome, or septic arthritis. *S. aureus* infections are caused by different strains including MSSA, MRSA, vancomycin-intermediate *S. aureus* (VISA), and vancomycin-resistant *S. aureus* (VRSA). *S. aureus* associated problems with infection are best known for MRSA, but any *S. aureus* infections can be dangerous and lethal. *E. faecium* and *E. faecalis*, are opportunistic pathogens. These bacteria can cause a variety of health problems including urinary tract, intra-abdominal, pelvic, and soft tissue infections, bacteremia, endocarditis, and several uncommon infections such as meningitis, septic arthritis, and pneumonia.

*S. aureus* along with other staphylococci are the most common causes of persistent biofilm-associated infections. These infections are inherently resistant to existing antibiotics and the host's immune system. *S. epidermidis* is an opportunistic pathogen, which causes the most biofilm-associated infections on indwelling medical devises and is the most frequent cause of nosocomial sepsis. Two percent of the population carry its drug-resistant variant, methicillin-resistant *S. aureus* (MRSA), and this bacterium causes the highest number of invasive infections among all antibiotic-resistant bacteria. The failure of antibiotic therapy against *S. aureus* is due to the development of multidrug-resistant strains and its ability to adopt a persistent non-growing lifestyle and forming biofilms. These features are associated with antibiotic resistance and persistent infection. Similarly, enterococci bacteria that are found in the human intestines and in the female genital tract can cause serious infections. These bacteria are constantly finding new ways to neutralize the effects of antibiotics and vancomycin-resistant enterococci (VRE) infections are becoming common.

Methods for inhibiting growth or proliferation of or killing a microbe are also provided. In some embodiments, administration of any of the compounds disclosed herein to a subject or contacting a microbe with the compound provides for inhibiting growth or proliferation of or killing the microbe.

As used herein, microbe or microorganism is an organism that may exist in a single-cell form or may refer to a colony of cells. Suitably, the microbe is a bacteria. In some embodiments, the bacteria is a Gram-positive bacteria, e.g., *S. aureus*, a *S. epidermidis, B. subtilis*, or *E. faecium*. In other embodiments, the bacteria is a Gram-negative bacteria, e.g., *A. baumannii*.

In some embodiments, the microbe is antimicrobial resistant. An antimicrobial resistant microbe is one that has become resistant to one or more antimicrobial agents that are approved for use in the treatment of a subject. Antimicrobial-resistant microbes are more difficult to treat, requiring higher doses, longer treatment regimens, or alternative medications which may prove more toxic. As demonstrated in the Examples, the presently disclosed compounds demonstrated antimicrobial activity against several antimicrobial-resistant microbes, including, *S. aureus* BAA-2312 (Sa12), which is methicillin resistant; *S. aureus* ATCC 33591 (Sa91), which is methicillin resistant; *S. aureus* ATCC 700699 (Sa99), which is methicillin resistant, oxacillin resistant, and has reduced vacncomycin susceptibility; *S. aureus* ATCC 33592 (Sa92), which is methicillin resistant and gentamicin resistant.

In some embodiments, the microbe is antimicrobial persister. Persisters are in a transient, metabolically inactive state. Microbes in this state make conventional antimicrobials that target essential cellular growth processes ineffective. This results in high clinical failure rates of antimicrobial chemotherapy. As demonstrated in the Examples, the presently disclosed compounds demonstrated antimicrobial activity against persisters, including, *S. aureus* ATCC 700699 (Sa99). Bacterial biofilms are small bacterial communities held together by an extracellular matrix. The biofilm matrix makes bacteria tolerant to harsh conditions and resistant to antibacterial treatments. Biofilms act as a dangerous reservoir of persisters, which can be a nidus for re-infection.

In some embodiments, the methods described herein are practiced in vivo. In other embodiments, the methods described herein are practiced in vitro or ex vivo.

As used herein the term "effective amount" refers to the amount or dose of the compound that provides the desired effect. In some embodiments, the effective amount is the amount or dose of the compound, upon single or multiple dose administration to the subject, which provides the desired effect in the subject under diagnosis or treatment. Suitably the desired effect may be inhibiting the growth or proliferation of or killing the microbe in the subject or reverse the progression or severity of resultant symptoms associated with the microbe.

An effective amount can be readily determined by those of skill in the art, including an attending diagnostician, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Example 1. Compound Synthesis

Synthesis of Epoxy Ketones

The electrophile, epoxynootkatone (2) was synthesized by reacting $H_2O_2$/NaOH with nootkatone (1) in quantitative yield (Scheme 1). Epoxy-ketones were synthesized according to a reported procedure.[27]

Synthesis of Fused-Thiazole

As illustrated in Scheme 1, a mixture of epoxynootkatone (2) (1 mmol) and thiourea or thioamide derivative (1.05 mmol) in acetic acid (5 ml) was heated to 100° C. in a round-bottom flask for 8 hrs. After finishing the reaction, the reaction mixture was cooled to room temperature and water was added to precipitate the product. The precipitate was filtered and washed repeatedly with water followed by drying in vacuo to get the pure product. In case of impurities, recrystallization with methanol afforded the pure products.

Reaction of phenyl thioacetamide with the epoxyketone (2) formed the product (3) in 76% yield. Another benzyl derivative (4) was obtained in 87% under the established condition. Aliphatic heterocycles, tetrahydropyran (5) and protected piperidine (6), were formed in 90% and 84% yields respectively. After the successful reaction of aliphatic thioamide, we reacted thiobenzamide derivatives with the electrophile (2). Reaction of the thiobenzamide formed the fused-thiazole product (7) in 76% yield. Alkyl substitution, methyl (8), and tert-butyl (9), on the phenyl ring afforded the product formation in an ~80% average yield. More electron donating groups such as ether on the phenyl ring formed the products (10, 11, and 12) efficiently. Very strong electron donating group such as hydroxyl did not hamper the product formation and ortho (13), meta (14), and para (15) products were isolated in 82%, 85%, and 71% respectively. Catechol derivative (16) was also obtained, albeit in low yield, 69%. Reaction of 3,4-(methylenedioxy)thiobenzamide with the electrophile formed the product (17) in 88% yield. After getting the product from electron donating groups, we reacted epoxy-nootkatone with electron-withdrawing substituted thiobenzamide derivatives. Moderately electron-withdrawing groups, halogens (fluoro, chloro, and bromo) formed the products (18, 19, and 20) in a good average yield. Difluoro-substituted product (21) was also obtained in 78% yield. Very strong electron withdrawing groups such as trifluoromethyl and nitro substituted products (22 and 23) were obtained in 68% and 88% yield respectively.

To further broaden the scope of our methodology and generate a library of novel molecules, we reacted the thiourea derivatives with the electrophile. We obtained the aminothiazole derivatives efficiently. Mono- and difluoro phenyl products (24 and 25) were obtained in 79% and 98% yield respectively. Trifluoromethoxy substituted product (26) formed in 60% yield. Very strong electron withdrawing substitutions on the phenyl ring also gave the expected products (27, 28, and 29) efficiently.

Exemplary Compounds

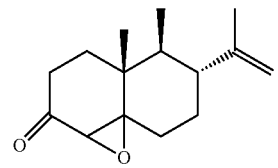

(1aS,4aS,8aR)-6-isopropenyl-4,4a-dimethyl-3,4,5,6,7,8-hexahydro-1aH-naphtho[1,8a-b]oxiren-2-one (EN)

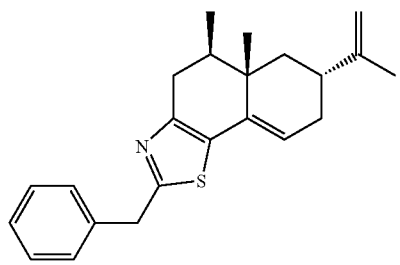

(5R,5aS,7R)-2-benzyl-7-isopropenyl-5,5a-dimethyl-5,6,7,8-tetrahydro-4H-benzo[g][1,3]benzothiazole (3). Light yellow solid (294 mg, 84%); $^1$H NMR (300 MHz, CDCl$_3$): δ 7.35-7.30 (m, 5H), 5.68 (dd, J=2.7, 5.1 Hz, 1H), 4.77 (s, 2H), 4.28 (s, 2H), 2.86 (dd, J=5.1, 17.2 Hz, 1H), 2.56 (dd, J=11.4, 17.0 Hz, 1H), 2.47-2.39 (m, 1H), 2.26 (dt, J=5.0, 18.4 Hz, 1H), 2.11-1.98 (m, 2H), 1.82-1.72 (m, 1H), 1.77 (s, 3H), 1.27 (t, J=12.6 Hz, 1H), 1.02 (d, J=6.5 Hz, 3H), 0.96 (s, 3H); $^{13}$C NMR (75 MHz, CDCl$_3$): δ 167.1, 149.6, 148.5, 137.2, 136.3, 131.6, 129.0, 128.8, 127.3, 122.0, 109.1, 40.0, 39.8, 39.5, 37.5, 36.9, 32.6, 31.1, 20.7, 17.2, 14.9. HRMS (ESI-FTMS Mass (m/z): calcd for C$_{23}$H$_{27}$NS [M+H]$^+$=350.1936, found 350.1943.

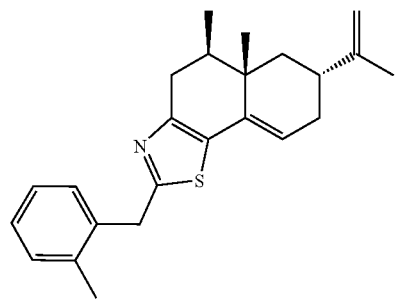

(5R,5aS,7R)-7-isopropenyl-5,5a-dimethyl-2-(o-tolylmethyl)-5,6,7,8-tetrahydro-4H-benzo[g][1,3]benzothiazole (4). White solid (318 mg, 87%); $^1$H NMR (300 MHz, CDCl$_3$): δ 7.26-7.20 (m, 5H), 5.64-5.63 (m, 1H), 4.75 (s, 2H), 4.26 (s, 2H), 2.84 (dd, J=4.8, 14.6 Hz, 1H), 2.60-2.50 (m, 1H), 2.32 (s, 3H), 2.25-2.19 (m, 1H), 2.05-1.98 (m, 1H), 1.75 (s, 5H), 124 (t, J=12.7 Hz, 1H), 1.01 (d, J=6.7 Hz, 3H), 0.94 (s, 3H); $^{13}$C NMR (75 MHz, CDCl$_3$): δ 167.5, 149.6, 148.4, 136.7, 136.3, 136.0, 131.7, 130.7, 130.0, 127.6, 126.3, 122.0, 109.0, 77.4, 40.0, 39.6, 37.5, 36.9, 32.6, 31.1, 20.7, 19.7, 17.1, 14.9. HRMS (ESI-FTMS Mass (m/z): calcd for $C_{24}H_{29}NS$ [M+H]$^+$=364.2093, found 364.2087.

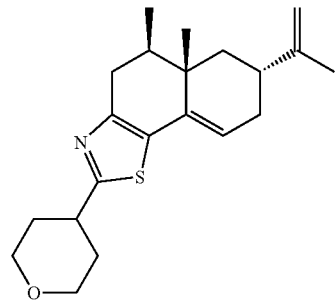

5

(5R,5aS,7R)-7-isopropenyl-5,5a-dimethyl-2-tetrahydropyran-4-yl-5,6,7,8-tetrahydro-4H-benzo[g][1,3]benzothiazole (5). White solid (310 mg, 90%); $^1$H NMR (300 MHz, CDCl$_3$): δ 5.77-5.74 (m, 1H), 4.78 (s, 2H), 4.02 (J, d=10.6 Hz, 2H), 3.53 (t, J=11.2 Hz, 2H), 3.23-2.15 (m, 1H), 2.78 (dd, J=16.9, 13.5 Hz, 1H), 2.60-2.35 (m, 2H), 2.28-2.22 (m, 2H), 2.00-1.96 (m, 4H), 1.85-1.74 (m, 5H), 123 (t, J=12.3 Hz, 1H), 0.97 (d, J=6.5 Hz, 3H), 0.92 (s, 3H); $^{13}$C NMR (75 MHz, CDCl$_3$): δ 171.4, 149.6, 148.5, 136.4, 130.2, 121.9, 109.0, 67.5, 40.1, 39.8, 39.7, 37.5, 36.9, 33.1, 32.8, 31.2, 20.7, 17.2, 14.9. HRMS (ESI-FTMS Mass (m/z): calcd for $C_{21}H_{29}NOS$ [M+H]$^+$=344.2042, found 344.2042.

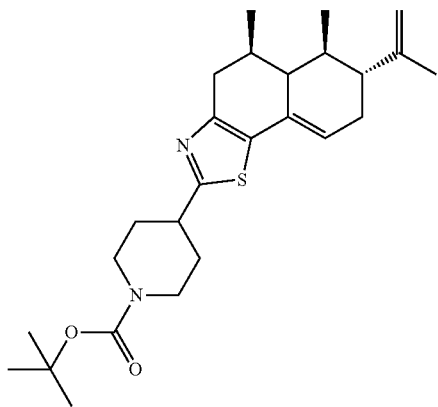

6 tert-Butyl 4-[(5R,5aS,7R)-7-isopropenyl-5,5a-dimethyl-5,6,7,8-tetrahydro-4H-benzo [g][1,3]benzothiazol-2-yl]cyclohexanecarboxylate (6). Beige solid (373 mg, 84%); $^1$H NMR (300 MHz, CDCl$_3$): δ 7.27 (s, 1H), 5.75-5.72 (m, 1H), 4.93 (s, 2H), 4.20 (br, 1H), 3.09-3.02 (m, 1H), 2.85-2.78 (m, 3H), 2.58-2.27 (m, 4H), 2.08-2.04 (m, 4H), 1.83-1.68 (m, 7H), 1.47 (s, 8H), 1.32-1.24 (m, 1H), 1.02 (d, J=6.8 Hz, 3H), 0.97 (s, 3H); $^{13}$C NMR (75 MHz, CDCl$_3$): δ 170.9, 154.7, 149.7, 148.9, 136.6, 130.1, 121.6, 109.0, 79.5, 43.9, 43.7, 40.9, 40.1, 39.7, 37.5, 36.9, 33.0, 32.4, 31.2, 28.4, 20.7, 17.2, 15.0. HRMS (ESI-FTMS Mass (m/z): calcd for $C_{26}H_{38}N_2O_2S$ [M+H]$^+$=443.2726, found 443.2716.

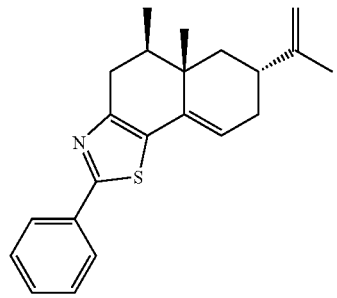

7

(5R,5aS,7R)-7-isopropenyl-5,5a-dimethyl-2-phenyl-5,6,7,8-tetrahydro-4H-benzo[g][1,3]benzothiazole (7). Dark red viscous (256 mg, 76%); $^1$H NMR (300 MHz, CDCl$_3$): δ 7.94-7.87 (m, 2H), 7.43-7.27 (m, 3H), 5.88-5.86 (m, 1H), 4.80 (s, 2H), 2.96 (dd, J=5.0, 14.6 Hz, 1H), 2.68-2.31 (m, 3H), 2.15-2.01 (m, 1H), 1.86-1.80 (m, 5H), 1.31 (t, J=12.1 Hz, 1H), 1.05 (d, J=6.7 Hz, 3H), 1.00 (s, 3H); $^{13}$C NMR (75 MHz, CDCl$_3$): δ 163.5, 150.1, 149.1, 136.1, 133.3, 131.0, 129.2, 128.3, 125.8, 121.9, 108.6, 39.1, 37.0, 36.4, 32.6, 30.8, 20.3, 16.7, 14.5. HRMS (ESI-FTMS Mass (m/z): calcd for $C_{22}H_{25}NS$ [M+H]$^+$=336.1780, found 336.1775.

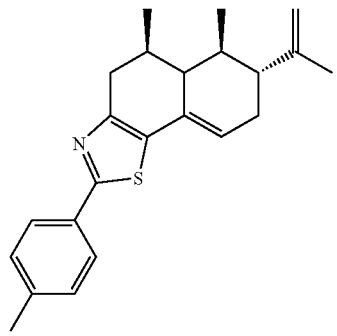

8

(5R,5aS,7R)-7-isopropenyl-5,5a-dimethyl-2-(p-tolyl)-5,6,7,8-tetrahydro-4H-benzo[g][1,3] benzothiazole (8). Light beige solid (267 mg, 76%); $^1$H NMR (300 MHz, CDCl$_3$): δ 7.80 (d, J=8.0 Hz, 2H), 7.24 (t, J=8.0 Hz, 2H), 5.84 (s, 1H), 4.80 (s, 2H), 2.94 (dd, J=5.0, 14.6 Hz, 1H), 2.64-2.58 (m, 1H), 2.49-2.31 (m, 5H), 2.19-2.05 (m, 1H), 1.86-1.80 (m, 5H), 1.22 (t, J=12.6 Hz, 1H), 1.05 (d, J=6.8 Hz, 3H), 1.01 (s, 3H); $^{13}$C NMR (75 MHz, CDCl$_3$): δ 164.3, 150.4, 149.7, 140.0, 136.7, 131.0, 129.5, 126.3, 122.2, 109.0, 40.1, 39.7, 37.5, 37.0, 33.1, 31.3, 23.3, 21.4, 20.7, 17.2, 15.0. HRMS (ESI-FTMS Mass (m/z): calcd for $C_{23}H_{27}NS$ [M+H]$^+$=350.1936, found 350.1937.

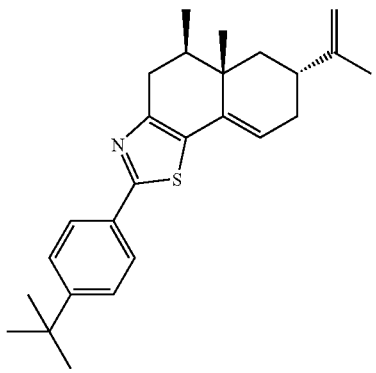

9

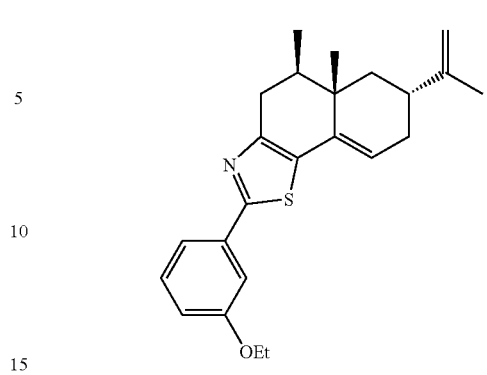

11

(5R,5aS,7R)-2-(4-tert-butylphenyl)-7-isopropenyl-5,5a-dimethyl-5,6,7,8-tetrahydro-4H-benzo[g][1,3]benzothiazole (9). Beige solid (326 mg, 83%); $^1$H NMR (300 MHz, CDCl$_3$): δ 7.86 (d, J=7.8 Hz, 2H), 7.44 (d, J=8.2 Hz, 2H), 5.85 (s, 1H), 4.79 (s, 2H), 3.00-2.95 (m, 1H), 2.68-2.30 (m, 3H), 2.14-2.01 (m, 1H), 1.79 (s, 5H), 1.34 (s, 10H), 1.04 (d, J=6.8 Hz, 3H), 1.00 (s, 3H); $^{13}$C NMR (75 MHz, CDCl$_3$): δ 164.4, 153.5, 149.8, 149.6, 136.5, 130.4, 126.3, 125.9, 122.5, 109.1, 40.0, 39.6, 37.5, 36.9, 34.9, 32.8, 31.2, 31.1, 20.7, 17.2, 14.9. HRMS (ESI-FTMS Mass (m/z): calcd for C$_{26}$H$_{33}$NS [M+H]$^+$=392.2406, found 392.2409.

(5R,5aS,7R)-2-(3-ethoxyphenyl)-7-isopropenyl-5,5a-dimethyl-5,6,7,8-tetrahydro-4H-benzo[g][1,3]benzothiazole (11). Light beige solid; (329 mg, 86%) $^1$H NMR (300 MHz, CDCl$_3$): δ 7.49 (t, J=7.8 Hz, 2H), 7.35-7.28 (m, 2H), 6.95 (d, J=7.4 Hz, 1H), 5.86-5.85 (m, 1H), 4.80 (s, 2H), 4.17-4.10 (m, 2H), 2.99-2.93 (m, 1H), 2.69-2.31 (m, 3H), 2.15-2.12 (m, 1H), 1.86-1.80 (m, 5H), 1.45 (t, J=6.9 Hz, 2H), 1.32 (t, J=12.4 Hz, 1H), 1.05 (d, J=6.7 Hz, 3H), 1.01 (s, 3H); $^3$C NMR (75 MHz, CDCl$_3$): δ 164.1, 159.3, 150.1, 149.6, 136.5, 134.5, 131.6, 129.9, 122.7, 119.0, 116.9, 111.6, 109.1, 63.7, 40.1, 39.6, 37.5, 36.9, 32.8, 31.3, 20.7, 17.2, 14.9, 14.8. HRMS (ESI-FTMS Mass (m/z): calcd for C$_{24}$H$_{29}$NOS [M+H]$^+$=380.2042, found 380.2041.

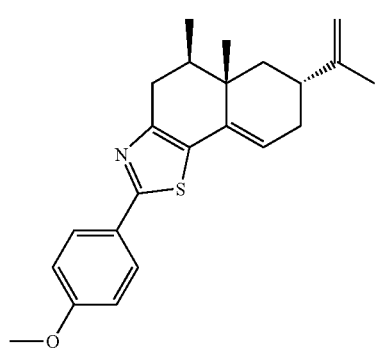

10

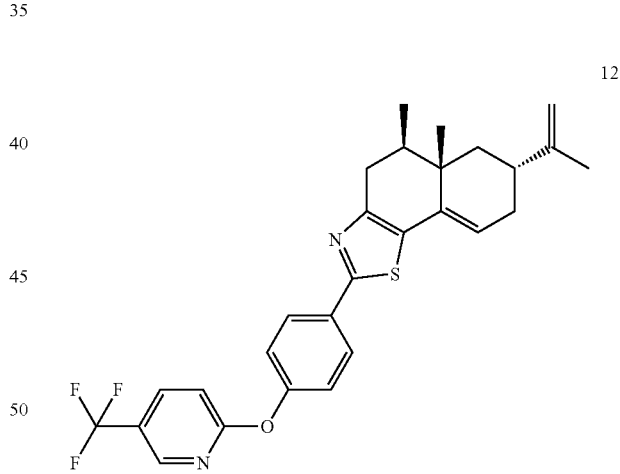

12

(5R,5aS,7R)-7-isopropenyl-2-(4-methoxyphenyl)-5,5a-dimethyl-5,6,7,8-tetrahydro-4H-benzo[g][1,3]benzothiazole (10). Beige solid (243 mg, 66%); $^1$H NMR (300 MHz, CDCl$_3$): δ 7.85 (d, J=8.7 Hz, 2H), 6.94 (d, J=8.7 Hz, 2H), 5.82-5.81 (m, 1H), 4.80 (s, 2H), 3.86 (s, 3H), 2.92 (dd, J=5.0, 14.6 Hz, 1H), 2.66-2.30 (m, 3H), 2.15-2.05 (m, 1H), 1.86-1.80 (m, 5H), 1.31 (t, J=12.6 Hz 1H), 1.05 (d, J=6.8 Hz, 3H), 1.01 (s, 3H); $^{13}$C NMR (75 MHz, CDCl$_3$): δ 164.0, 160.8, 150.4, 149.8, 136.7, 130.6, 127.8, 126.8, 121.9, 114.1, 109.0, 55.4, 40.1, 39.7, 37.5, 36.9, 33.1, 31.2, 20.7, 17.2, 15.0. HRMS (ESI-FTMS Mass (m/z): calcd for C$_{23}$H$_{27}$NOS [M+H]$^+$=366.1886, found 366.1885.

(5R,5aS,7R)-7-isopropenyl-5,5a-dimethyl-2-[4-[[5-(trifluoromethyl)-2-pyridyl]oxy]phenyl]-5,6,7,8-tetrahydro-4H-benzo[g][1,3]benzothiazole (12). Light beige solid (466 mg, 93%); $^1$H NMR (300 MHz, CDCl$_3$): δ 8.47 (s, 1H), 8.03-7.93 (m, 2H), 7.28-7.17 (m, 3H), 7.06 (t, J=8.5 Hz, 1H), 5.88-5.87 (m, 1H), 4.81-4.76 (m, 2H), 3.00-2.94 (m, 1H), 2.70-2.16 (m, 3H), 2.12-2.02 (m, 1H), 1.86-1.76 (m, 5H), 1.33 (t, J=12.8 Hz, 1H), 1.08-0.98 (m, 6H); $^{13}$C NMR (75 MHz, CDCl$_3$): δ 165.3, 163.2, 154.5, 149.6, 145.4 ($^3J_{C-F}$=4.3) 136.9 ($^3J_{C-F}$=3.2), 136.4, 131.7, 128.1, 123.0, 121.9 ($^2J_{C-F}$ 33.0), 121.9, 111.6, 109.1, 70.4, 40.0, 39.6, 37.6, 36.9, 32.8, 31.3, 27.1, 20.7, 17.3, 14.9. HRMS (ESI-FTMS Mass (m/z): calcd for $C_{28}H_{27}F_3N_2OS$ [M+H]$^+$=497.1868, found 497.1865.

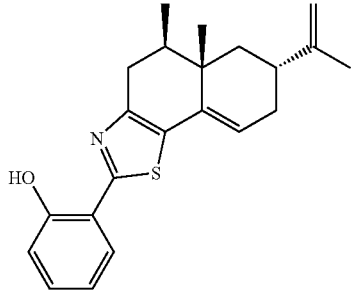

2-[(5R,5aS,7R)-7-isopropenyl-5,5a-dimethyl-5,6,7,8-tetrahydro-4H-benzo[g][1,3]benzothiazol-2-yl]phenol (13). Light red solid; (289 mg, 82%) $^1$H NMR (300 MHz, CDCl$_3$): δ 7.59 (d, J=7.7 Hz, 1H), 7.88 (t, J=8.5 Hz, 2H), 7.05 (d, J=8.28 Hz, 1H), 6.88 (t, J=7.5 Hz, 1H), 5.89-5.86 (m, 1H), 4.81 (s, 2H), 2.92 (dd, J=4.7, 14.7 Hz, 1H), 2.65-2.32 (m, 3H), 2.16-2.06 (m, 1H), 1.87-1.81 (m, 5H), 1.32 (t, J=12.6 Hz, 1H), 1.06 (d, J=6.8 Hz, 3H), 1.01 (s, 3H); $^{13}$C NMR (75 MHz, CDCl$_3$): δ 164.9, 156.9, 149.5, 147.9, 136.0, 131.3, 129.7, 127.1, 123.2, 119.3, 117.6, 117.0, 109.1, 40.0, 39.5, 37.6, 36.9, 32.4, 31.3, 20.7, 17.2, 14.9. HRMS (ESI-FTMS Mass (m/z): calcd for C22H25NOS [M+H]$^+$=352.1729, found 352.1725.

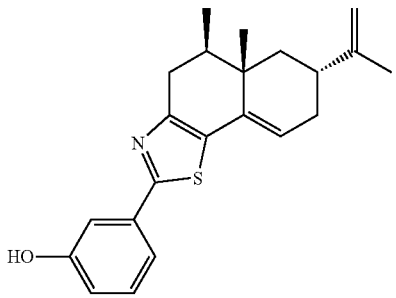

3-[(5R,5aS,7R)-7-isopropenyl-5,5a-dimethyl-5,6,7,8-tetrahydro-4H-benzo[g][1,3]benzothiazol-2-yl]phenol (14). White solid; (301 mg, 85%) $^1$H NMR (300 MHz, CDCl$_3$): δ 7.54 (s, 1H), 7.39-7.23 (m, 3H), 6.91 (d, J=7.9 Hz, 1H), 5.86 (s, 1H), 4.80 (s, 2H), 2.98-2.92 (m, 1H), 2.67-2.31 (m, 3H), 2.15-2.11 (m, 1H), 1.80 (s, 5H), 1.31 (t, J=12.3 Hz, 1H), 1.05-1.00 (m, 6H); $^{13}$C NMR (75 MHz, CDCl$_3$): δ 164.4, 156.6, 149.7, 149.5, 136.3, 134.1, 131.7, 130.2, 123.0, 118.8, 117.7, 113.2, 109.1, 40.0, 39.5, 37.5, 36.9, 32.5, 31.3, 20.7, 17.2, 14.9. HRMS (ESI-FTMS Mass (m/z): calcd for $C_{22}H_{25}NOS$ [M+H]$^+$=352.1729, found 352.1727.

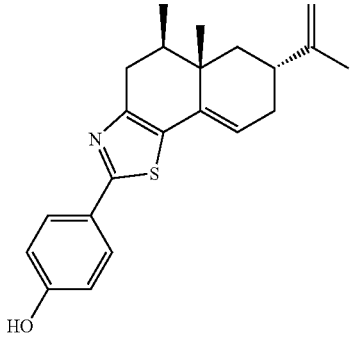

4-[(5R,5aS,7R)-7-isopropenyl-5,5a-dimethyl-5,6,7,8-tetrahydro-4H-benzo[g][1,3]benzothiazol-2-yl]phenol (15). Dark brown solid; (252 mg, 71%) $^1$H NMR (300 MHz, CDCl$_3$): δ 7.72 (d, J=8.5 Hz, 2H), 6.80 (d, J=8.5 Hz, 2H), 5.84-5.81 (m, 1H), 4.80 (s, 2H), 2.91 (dd, J=12.3, 11.1 Hz, 1H), 2.65-2.31 (m, 3H), 2.14-2.02 (m, 1H), 1.85-1.80 (m, 5H), 1.31 (t, J=12.6 Hz, 1H), 1.03 (d, J=6.8 Hz, 3H), 1.00 (s, 3H); $^{13}$C NMR (75 MHz, CDCl$_3$): δ 165.5, 158.9, 149.6, 136.4, 130.5, 128.2, 125.0, 122.2, 116.0, 109.0, 84.6, 40.1, 39.6, 37.5, 36.9, 32.5, 31.2, 20.7, 17.2, 14.9. HRMS (ESI-FTMS Mass (m/z): calcd for $C_{22}H_{25}NOS$ [M+H]$^+$=352.1729, found 352.1732.

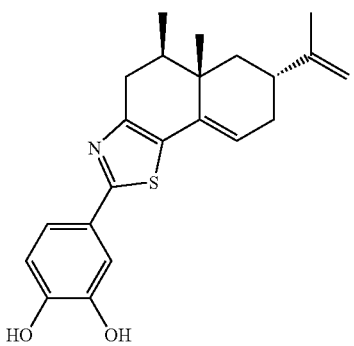

5-[(5R,5aS,7R)-7-isopropenyl-5,5a-dimethyl-5,6,7,8-tetrahydro-4H-benzo[g][1,3]benzothiazol-2-yl]benzene-1,3-diol (16). Brown solid (257 mg, 69%); $^1$H NMR (300 MHz, DMSO-d$_6$): δ 9.49 (s, 1H), 9.34 (s, 1H), 7.29 (s, 1H), 7.15 (d, J=7.02 Hz, 1H), 6.78 (d, J=7.8 Hz, 1H), 5.72 (s, 1H), 4.74 (d, J=8.5 Hz, 2H), 2.77 (d, J=13.4 Hz, 1H), 2.49-2.22 (m, 3H), 2.04-1.95 (m, 1H), 1.71 (s, 5H), 1.20 (t, J=12.3 Hz, 1H), 0.95 (d, J=6.3 Hz, 3H), 0.90 (s, 3H); $^{13}$C NMR (75 MHz, DMSO-d$_6$): δ 164.2, 149.7, 149.5, 148.6, 146.1, 136.3, 129.6, 124.5, 122.4, 118.6, 116.5, 113.6, 109.7, 102.8, 49.0, 37.4, 36.7, 32.7, 31.1, 21.0, 17.5, 15.1. HRMS (ESI-FTMS Mass (m/z): calcd for $C_{22}H_{25}NO_2S$ [M+H]$^+$=368.1678, found 368.1684.

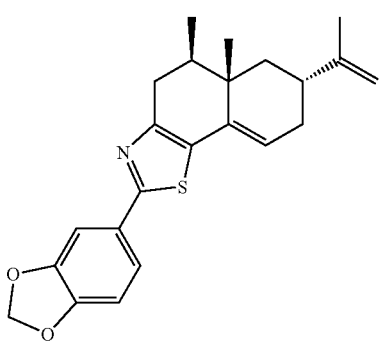

(5R,5aS,7R)-2-(1,3-benzodioxol-5-yl)-7-isopropenyl-5,5a-dimethyl-5,6,7,8-tetrahydro-4H-benzo[g][1,3]benzothiazole (17). Brown solid; (366 mg, 88%) $^1$H NMR (300 MHz, CDCl$_3$): δ 7.44 (s, 2H), 6.87-6.83 (m, 1H), 6.01 (d, J=7.7 Hz, 2H), 5.81 (s, 1H), 4.80 (s, 2H), 2.96-2.90 (m, 1H), 2.66-2.30 (m, 3H), 2.14-2.02 (m, 1H), 1.80-1.78 (s, 5H), 1.31 (t, J=12.6 Hz, 1H), 1.06-0.99 (m, 6H); $^{13}$C NMR (75 MHz, CDCl$_3$): δ 163.9, 151.0, 149.6, 148.2, 136.4, 130.8, 122.5, 121.2, 109.1, 108.6, 107.6, 106.7, 101.9, 101.6, 40.0, 39.6, 37.5, 36.9, 32.8, 31.2, 20.7, 17.2, 14.9. HRMS (ESI-FTMS Mass (m/z): calcd for $C_{23}H_{25}NO_2S$ [M+H]$^+$=380.1678, found 380.1672.

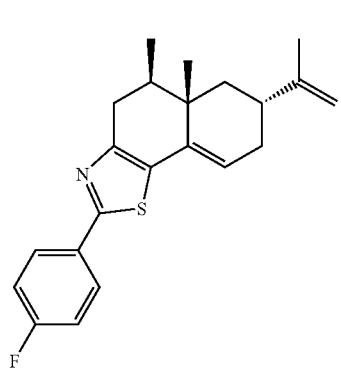

(5R,5aS,7R)-2-(4-fluorophenyl)-7-isopropenyl-5,5a-dimethyl-5,6,7,8-tetrahydro-4H-benzo[g][1,3]benzothiazole (18). Light beige solid; (275 mg, 77%) $^1$H NMR (300 MHz, CDCl$_3$): δ 7.90 (q, J=8.6 Hz, 2H), 7.11 (t, J=8.5 Hz, 2H), 5.86-5.85 (m, 1H), 4.80 (s, 2H), 2.92 (dd, J=12.1, 11.1 Hz, 1H), 2.67-2.31 (m, 3H), 2.15-2.11 (m, 1H), 1.86-1.80 (m, 5H), 1.32 (t, J=12.6 Hz, 1H), 1.06 (d, J=6.8 Hz, 3H), 1.01 (s, 3H); $^{13}$C NMR (75 MHz, CDCl$_3$): δ 163.7 (d, $^1J_{C-F}$=248.9 Hz), 162.8, 150.5, 149.6, 136.5, 131.6, 130.0, 128.2 (d, $^3J_{C-F}$=8.3 Hz), 122.6, 115.9 (d, $^2J_{C-F}$=21.8), 109.1, 40.1, 39.6, 37.5, 36.9, 33.0, 31.3, 20.7, 17.2, 15.0. HRMS (ESI-FTMS Mass (m/z): calcd for $C_{22}H_{24}FNS$ [M+H]$^+$=354.1686, found 354.1684.

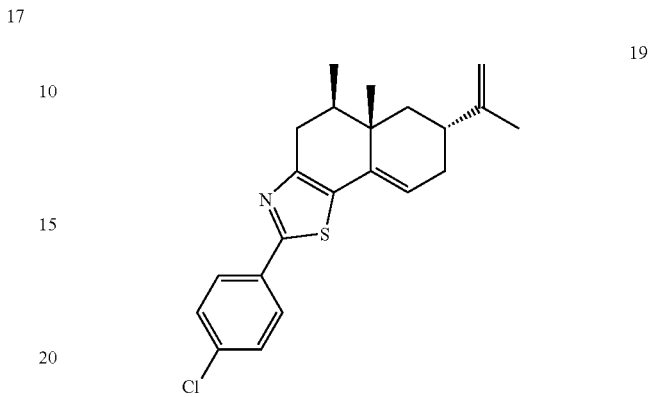

(5R,5aS,7R)-2-(4-chlorophenyl)-7-isopropenyl-5,5a-dimethyl-5,6,7,8-tetrahydro-4H-benzo[g][1,3]benzothiazole (19). Light beige solid; (286 mg, 77%) $^1$H NMR (300 MHz, CDCl$_3$): δ 7.84 (d, J=8.3 Hz, 2H), 7.38 (d, J=8.4 Hz, 2H), 5.86 (s, 1H), 4.79 (s, 2H), 2.96-2.90 (m, 1H), 2.67-2.30 (m, 3H), 2.15-2.11 (m, 1H), 1.85-1.79 (m, 5H), 1.31 (t, J=12.8 Hz, 1H), 1.04 (d, J=6.7 Hz, 3H), 1.00 (s, 3H); $^{13}$C NMR (75 MHz, CDCl$_3$): δ 162.6, 150.7, 149.6, 136.5, 135.6, 132.2, 131.9, 129.0, 127.5, 122.8, 109.1, 40.1, 39.6, 37.5, 36.9, 33.0, 31.3, 20.7, 17.2, 15.0. HRMS (ESI-FTMS Mass (m/z): calcd for $C_{22}H_{24}ClNS$ [M+H]$^+$=370.1390, found 370.1384.

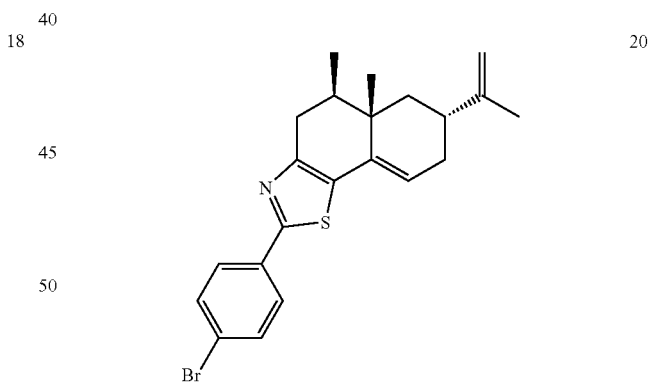

(5R,5aS,7R)-2-(4-bromophenyl)-7-isopropenyl-5,5a-dimethyl-5,6,7,8-tetrahydro-4H-benzo[g][1,3]benzothiazole (20). Yellow solid (377 mg, 90%); $^1$H NMR (300 MHz, CDCl$_3$): δ 7.79 (d, J=8.4 Hz, 2H), 7.55 (d, J=8.1 Hz, 2H), 5.87-5.86 (m, 1H), 4.79 (s, 2H), 2.97-2.92 (m, 1H), 2.67-2.30 (m, 3H), 2.14-2.10 (m, 1H), 1.85-1.79 (m, 5H), 1.31 (t, J=12.4 Hz, 1H), 1.05 (d, J=6.7 Hz, 31H), 1.00 (s, 3H); $^{13}$C NMR (75 MHz, CDCl$_3$): δ 162.6, 150.6, 149.6, 136.5, 132.5, 132.0, 127.8, 124.0, 123.0, 120.5, 109.1, 40.1, 39.6, 37.5, 36.9, 32.9, 31.3, 20.7, 17.2, 14.9. HRMS (ESI-FTMS Mass (m/z): calcd for $C_{22}H_{24}BrNS$ [M+H]$^+$=414.0885, found 414.0883.

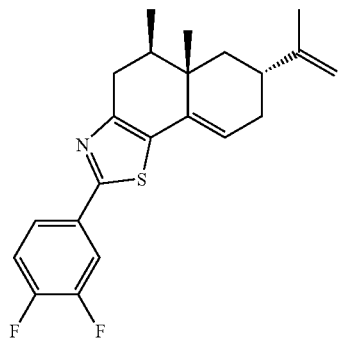

(5R,5aS,7R)-2-(3,4-difluorophenyl)-7-isopropenyl-5,5a-dimethyl-5,6,7,8-tetrahydro-4H-benzo[g][1,3]benzothiazole (21). Light yellow solid (291 mg, 78%); $^1$H NMR (300 MHz, CDCl$_3$): δ 7.78 (t, J=8.7 Hz, 1H), 7.64 (br, 1H), 7.28-7.17 (m, 1H), 5.88-5.86 (m, 1H), 4.80 (s, 2H), 2.96 (dd, J=4.9, 14.7 Hz, 1H), 2.67-2.32 (m, 3H), 2.16-2.06 (m, 1H), 1.86-1.80 (m, 5H), 1.31 (t, J=12.6 Hz, 1H), 1.06 (d, J=6.8 Hz, 3H), 1.00 (s, 3H); $^{13}$C NMR (75 MHz, CDCl$_3$): δ 161.4, 151.4 (dd, $J_{C-F}$=12.5, 244.4 Hz), 150.6 (dd, $J_{C-F}$=12.8, 241.1 Hz), 150.5, 149.5, 136.3, 132.6, 130.6, 123.2, 122.7 (dd, $J_{C-F}$=14.2, 18.2 Hz), 117.8 (d, $^2J_{C-F}$=17.8 Hz), 115.3 (d, $^2J_{C-F}$=19.0 Hz), 109.1, 40.0, 39.5, 37.6, 36.9, 32.8, 31.3, 20.7, 17.2, 14.9. HRMS (ESI-FTMS Mass (m/z): calcd for $C_{22}H_{23}F_2NS$ [M+H]$^+$=372.1592 found 72.1584.

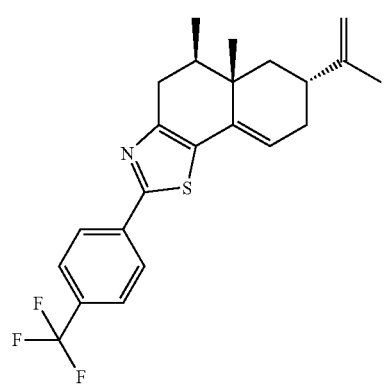

(5R,5aS,7R)-7-isopropenyl-5,5a-dimethyl-2-[4-(trifluoromethyl)phenyl]-5,6,7,8-tetra-tetrahydro-4H-benzo[g][1,3] benzothiazole (22). Light beige solid; (278 mg, 68%) $^1$H NMR (300 MHz, CDCl$_3$): δ 8.02 (d, J=8.2 Hz, 2H), 7.67 (d, J=8.4 Hz, 2H), 5.91-5.89 (m, 1H), 4.81 (s, 2H), 2.99-2.91 (dd, J=5.1, 14.6 Hz, 1H), 2.69-2.32 (m, 3H), 2.16-2.12 (m, 1H), 1.87-1.81 (m, 5H), 1.32 (t, J=12.6 Hz, 1H), 1.06 (d, J=6.8 Hz, 3H), 1.01 (s, 3H); $^{13}$C NMR (75 MHz, CDCl$_3$): δ 161.8, 151.3, 149.5, 137.0, 136.5, 132.8, 131.3 ($^2J_{C-F}$=32.4 Hz), 126.4, 125.9 ($^3J_{C-F}$=3.5 Hz), 124.4 ($^1J_{C-F}$=270.3 Hz), 123.3, 109.1, 40.1, 39.6, 37.5, 36.9, 33.1, 31.3, 20.7, 17.2, 15.0. HRMS (ESI-FTMS Mass (m/z): calcd for $C_{23}H_{24}F_3NS$ [M+H]$^+$=404.1654, found 404.1648.

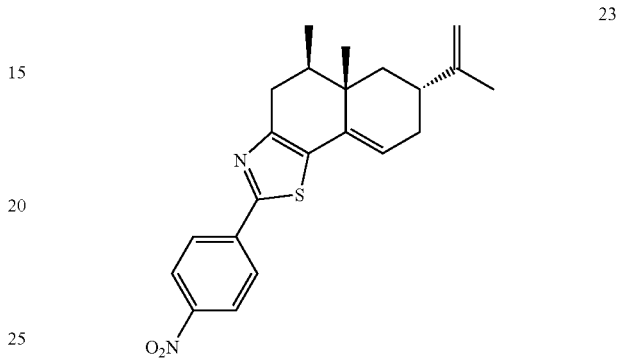

(5R,5aS,7R)-7-isopropenyl-5,5a-dimethyl-2-(4-nitrophenyl)-5,6,7,8-tetrahydro-4H-benzo [g][1,3]benzothiazole (23). Light orange solid; (367 mg, 88%) $^1$H NMR (300 MHz, CDCl$_3$): δ 8.29 (d, J=8.8 Hz, 2H), 8.09 (d, J=8.8 Hz, 2H), 5.96-5.95 (m, 1H), 4.81 (s, 2H), 2.92 (dd, J=5.0, 14.7 Hz, 1H), 2.71-2.33 (m, 3H), 2.17-2.02 (m, 1H), 1.88-1.81 (m, 5H), 1.32 (t, J=12.5 Hz, 1H), 1.07 (d, J=6.7 Hz, 3H), 1.01 (s, 3H); $^{13}$C NMR (75 MHz, CDCl$_3$): δ 160.6, 151.6, 149.4, 148.0, 139.0, 136.3, 134.2, 126.8, 124.4, 124.3, 109.2, 40.0, 39.5, 37.6, 36.8, 32.9, 31.4, 20.7, 17.2, 14.9. HRMS (ESI-FTMS Mass (m/z): calcd for $C_{22}H_{24}N_2O_2S$ [M+H]$^+$=381.1631, found 381.1634.

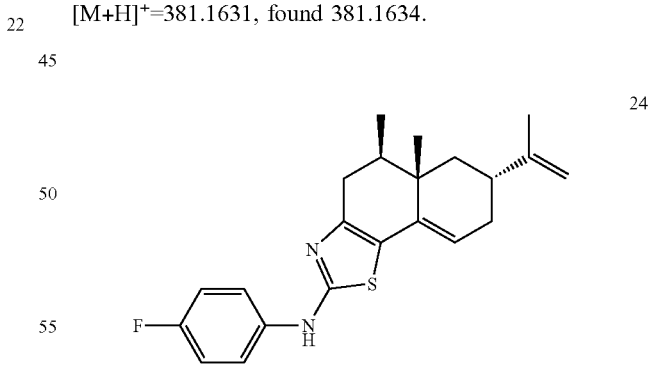

(5R,5aS,7R)—N-(4-fluorophenyl)-7-isopropenyl-5,5a-dimethyl-5,6,7,8-tetrahydro-4H-benzo[g][1,3]benzothiazol-2-amine (24). Whitish (292 mg, 79%); $^1$H NMR (300 MHz, DMSO-d$_6$): δ 7.36-7.31 (m, 2H), 7.05 (t, J=2.1 Hz, 2H), 5.47-5.45 (m, 1H), 4.77 (m, 2H), 2.66-2.58 (m, 1H), 2.45-2.24 (m, 3H), 2.12-1.99 (m, 1H), 1.81-1.78 (m, 5H), 1.28 (t, J=3.1 Hz, 1H), 0.99-0.98 (m, 6H); $^{13}$C NMR (75 MHz, DMSO-$d_6$): δ 163.1, 159.0 (d, $^1J$=241.4 Hz), 149.9, 145.5, 136.7, 136.5 (d, $^4J$=2.6 Hz), 121.3 (d, $^3J$=7.9 Hz), 120.0, 118.4, 116.1 (d, $^2J$=22.5 Hz), 108.9, 40.0, 39.6, 37.5, 37.0, 33.0, 31.0, 20.7, 17.3, 14.9. HRMS (ESI-FTMS Mass (m/z): calcd for $C_{22}H_{25}FN_2S$ [M+H]$^+$=369.1795 found 369.1795.

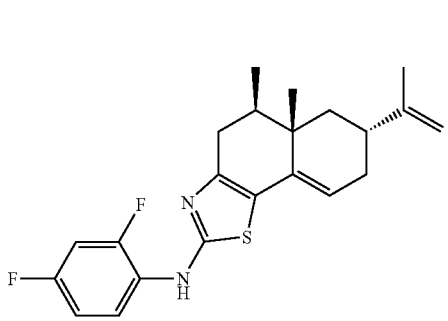

(5R,5aS,7R)—N-(2,4-difluorophenyl)-7-isopropenyl-5,5a-dimethyl-5,6,7,8-tetrahydro-4H-benzo[g][1,3]benzothiazol-2-amine (25). Brown; (380 mg, 98%) $^1$H NMR (300 MHz, DMSO-$d_6$): δ 7.99-7.91 (m, 1H), 6.93-6.86 (m, 2H), 5.50-5.47 (m, 1H), 4.78 (s, 2H), 2.70-2.62 (m, 1H), 2.48-2.23 (m, 3H), 2.14-1.99 (m, 1H), 1.83-1.78 (m, 5H), 1.33-1.08 (m, 2H), 1.01-0.99 (m, 6H); $^{13}$C NMR (75 MHz, DMSO-$d_6$): δ 161.5, 157.9 (dd, J=11.1, 243.5 Hz), 152.6 (dd, J=11.8, 245.5 Hz), 150.9, 145.6, 136.5, 125.2 (dd, J=7.47 Hz), 120.9, 119.0, 111.2 (dd, J=17.9 Hz), 108.9, 104.2 (d, $^2J$=23.0 Hz), 103.8 (d, $^2J$=22.9 Hz), 40.0, 39.5, 37.5, 37.0, 32.9, 31.0, 20.7, 17.3, 14.9. HRMS (ESI-FTMS Mass (m/z): calcd for $C_{22}H_{24}F_2N_2S$ [M+H]$^+$=387.1701 found 387.1706.

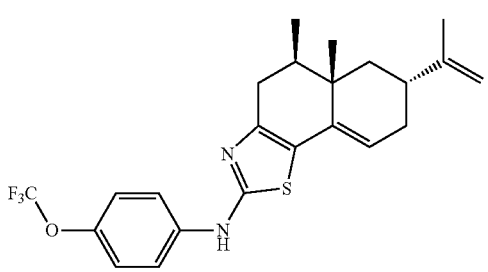

(5R,5aS,7R)-7-isopropenyl-5,5a-dimethyl-N-[4-(trifluoromethoxy)phenyl]-5,6,7,8-tetrahydro-4H-benzo[g][1,3]benzothiazol-2-amine (26). Whitish; (130 mg, 30%) $^1$H NMR (300 MHz, DMSO-$d_6$): δ 7.42-7.37 (m, 2H), 7.22-7.06 (m, 2H), 5.53-5.50 (m, 1H), 4.84 (s, 2H), 2.71-2.62 (m, 1H), 2.49-2.25 (m, 3H), 2.14-1.96 (m, 1H), 1.82-1.79 (m, 5H), 1.34-1.16 (m, 1H), 1.02-0.95 (m, 6H); $^{13}$C NMR (75 MHz, DMSO-$d_6$): δ 161.4, 149.8, 145.6, 144.2, 139.1, 136.6, 122.2, 120.7, 119.3, 118.9, 108.9, 40.0, 39.6, 37.5, 37.0, 33.0, 31.0, 20.7, 17.3, 14.9. HRMS (ESI-FTMS Mass (m/z): calcd for $C_{23}H_{25}F_3N_2OS$ [M+H]$^+$=435.1712 found 435.1711.

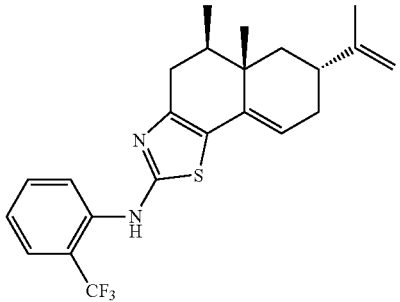

(5R,5aS,7R)-7-isopropenyl-5,5a-dimethyl-N-[2-(trifluoromethyl)phenyl]-5,6,7,8-tetrahydro-4H-benzo[g][1,3]benzothiazol-2-amine (27). Whitish; (218 mg, 52%) $^1$H NMR (300 MHz, DMSO-$d_6$): δ 8.05-8.02 (m, 1H), 7.69-7.53 (m, 2H), 7.07 (t, J=8.0 Hz, 1H), 5.53-5.51 (m, 1H), 4.79 (s, 2H), 2.75-2.67 (m, 1H), 2.52-2.42 (m, 2H), 2.33-2.24 (m, 1H), 2.10-2.01 (m, 1H), 1.85-1.77 (m, 5H), 1.32 (t, J=4.8 Hz, 1H), 1.03-0.99 (m, 6H); $^{13}$C NMR (75 MHz, DMSO-$d_6$): δ 160.8, 149.8, 145.4, 138.3, 136.4, 133.2, 126.8-126.6 (m), 124.0 (q, J=271.0 Hz), 121.8, 120.8, 119.4, 108.9. HRMS (ESI-FTMS Mass (m/z): calcd for $C_{23}H_{25}F_3N_2S$ [M+H]$^+$=419.1763 found 419.1763.

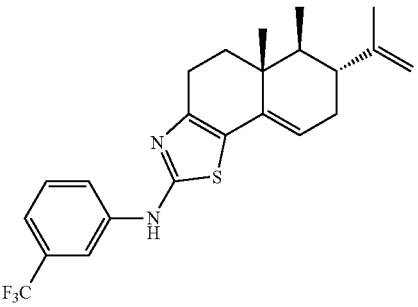

(5aR,6S,7R)-7-isopropenyl-5a,6-dimethyl-N-[3-(trifluoromethyl)phenyl]-5,6,7,8-tetrahydro-4H-benzo[g][1,3]benzothiazol-2-amine (28). Whitish; (412 mg, 98%) $^1$H NMR (300 MHz, DMSO-$d_6$): δ 7.63-7.59 (m, 2H), 7.46 (t, J=7.9 Hz, 1H), 7.31-7.28 (m, 1H), 5.55-5.53 (m, 1H), 4.79 (s, 2H), 2.73-2.65 (m, 1H), 2.51-2.41 (m, 2H), 2.34-2.27 (m, 1H), 2.15-2.01 (m, 1H), 1.83-1.76 (m, 5H), 1.50-0.99 (m, 8H); $^{13}$C NMR (75 MHz, DMSO-$d_6$): δ 161.0, 149.8, 145.5, 140.9, 136.5, 132.3-131.0 (m), 129.9, 123.8 (m, J=270.8 Hz), 121.0, 120.9, 119.2-119.0 (m), 114.9-114.8 (m), 108.9, 40.0, 39.6, 37.5, 37.0, 33.0, 31.0, 20.7, 17.3, 14.8. HRMS (ESI-FTMS Mass (m/z): calcd for $C_{23}H_{25}F_3N_2S$ [M+H]$^+$=419.1763 found 419.1764.

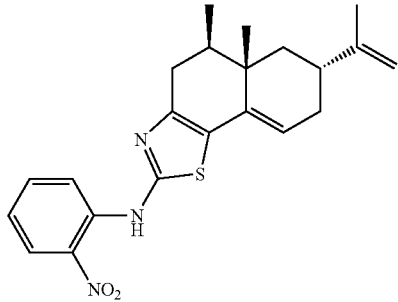

(5R,5aS,7R)-7-isopropenyl-5,5a-dimethyl-N-(2-nitrophenyl)-5,6,7,8-tetrahydro-4H-benzo[g][1,3]benzothiazol-2-amine (29). Red; (352 mg, 89%) $^1$H NMR (300 MHz, DMSO-d$_6$): δ 8.72-8.69 (m, 1H), 8.28-8.24 (m, 1H), 7.66-7.60 (m, 1H), 7.05-6.99 (m, 1H), 5.64-5.61 (m, 1H), 4.79 (s, 2H), 2.82-2.75 (m, 1H), 2.57-2.44 (m, 2H), 2.36-2.29 (m, 1H), 2.12-2.02 (m, 1H), 1.87-1.77 (m, 5H), 1.63 (br s, 1H), 1.27 (t, J=3.1 Hz, 1H), 1.05-1.02 (m, 6H); $^{13}$C NMR (75 MHz, DMSO-d$_6$): δ 157.7, 149.7, 146.6, 137.9, 136.3, 133.9, 126.2, 124.3, 120.7, 120.4, 119.1 109.0, 40.0, 39.6, 37.5, 36.9, 33.2, 31.1, 20.7, 17.3, 14.9, 14.5. HRMS (ESI-FTMS Mass (m/z): calcd for $C_{22}H_{25}N_3O_2S$ [M+H]$^+$=396.1740 found 396.1743.

Example 2. Antimicrobial Activity

Compounds prepared by the methods described herein were tested for their potency against 19 strains of Gram-positive and Gram-negative bacteria. Compound 15 showed activity against S. aureus strains with minimum inhibitory concentration (MIC) value as low as 6.25 μg/ml. This potent molecule also inhibited the growth of S. epidermidis and B. subtilis at MIC value 6.25 μg/ml. The inhibition of E. faecium strain was inhibited significantly with MIC value 3.125 μg/ml. Catechol-derived fused thiazole derivative (16) showed better activity against three S. aureus with an MIC value as low as 3.125 μg/ml. This compound inhibited the growth S. epidermidis efficiently with an MIC value of 3.125 μg/ml. This compound also showed very potent activity against E. faecium with MIC value as low as 1.56 μg/ml. Compound 17 showed moderate activity against two MRSA strains.

TABLE 1

Antimicrobial activities of compounds (3-29) against Gram-positive bacteria antibiotic susceptible strain; S. aureus ATCC 25923 (Sa23), and antibiotic-resistant strains: S. aureus BAA-2312 (Sa12), S. aureus ATCC 33591 (Sa91), S. aureus ATCC 700699 (Sa99), S. aureus ATCC 33592 (Sa92), S. epidermidis 700296 (Se), B. subtilis ATCC 6623 (Bs); Enterococcus faecalis ATCC 29212 (Es12), Enterococcus faecium ATCC 700221 (Em21); VC = vancomycin (positive control); and NA = no activity up to 100 μg/ml.

| # | Sa99 | Sa23 | Sa12 | Sa92 | Sa91 | Se | Bs | Es12 | Em21 |
|---|---|---|---|---|---|---|---|---|---|
| 3 | NA | NA | NA | NA | NA | NA | NA | NA | NA |
| 4 | NA | NA | NA | NA | NA | NA | NA | NA | NA |
| 5 | NA | 100 | 100 | 100 | NA | NA | 50 | NA | NA |
| 6 | NA |  | NA | NA | NA | NA | 100 | NA | NA |
| 7 | NA |  | NA | NA | NA | NA | NA | NA | NA |
| 8 | NA | 100 | NA | NA | NA | NA | NA | NA | NA |
| 9 | NA |  | NA | NA | NA | NA | NA | NA | NA |
| 10 | NA | 50 | 100 | NA | 100 | NA | 50 | NA | NA |
| 11 | NA | 50 | NA | NA | NA | NA | NA | NA | NA |
| 12 | NA |  | NA | NA | NA | NA | NA | NA | NA |
| 13 | NA | 50 | 100 | NA | 100 | NA | 50 | NA | NA |
| 14 | NA | 50 | NA | NA | NA | NA | NA | NA | NA |
| 15 | 12.5 | NA | 12.5 | 6.25 | 6.2 | 6.25 | 6.25 | 12.5 | 3.12 |
| 16 | 3.12 | 3.12 | 3.12 | 3.12 | 6.25 | 25 | 12.5 | 12.5 | 1.56 |
| 17 | NA | NA | NA | NA | 25 | 25 | 12.5 | NA | NA |
| 18 | NA | NA | 25 | NA | 50 | NA | NA | NA | NA |
| 19 | 25 | 25 | 25 | NA | 50 | 50 | 12.5 | NA | NA |
| 20 | NA | NA | NA | NA | 50 | NA | NA | NA | NA |
| 21 | NA | 100 | NA | 1.56 | NA | NA | NA | NA | NA |
| 22 | NA |  | NA | NA | NA | NA | NA | NA | NA |
| 23 | NA |  | NA | NA | NA | NA | NA | NA | NA |
| 24 | NA | 50 | NA | NA | NA | NA | 100 | NA | NA |
| 25 | NA | 100 | NA | NA | NA | NA | NA | NA | NA |
| 26 | NA | 50 | NA | NA | NA | NA | 100 | NA | NA |
| 27 | NA |  | NA | NA | NA | NA | NA | NA | NA |
| 28 | NA |  | NA | NA | NA | NA | NA | NA | NA |
| 29 | NA |  | NA | NA | NA | NA | NA | NA | NA |
| VC | 0.78 | 3.125 | 0.78 | 1.56 | 1.56 | 1.56 | 0.39 | 3.12 | NA |

Figure 2:
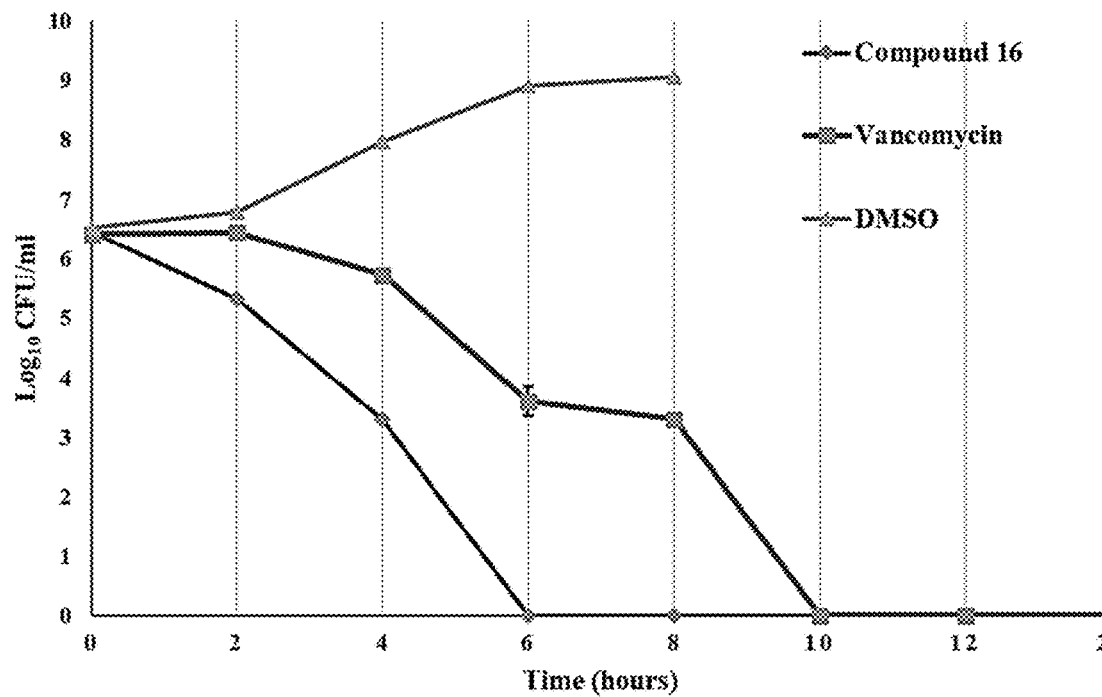
FIG. 2: Time Kill Assay of compound 16 at 4×MIC. Vancomycin and DMSO are positive and negative controls respectively.

In time kill assay studies, compound 16 was found to be bactericidal and it eliminated bacteria at 6 hours (FIG. 2). The positive control vancomycin eliminated bacteria at 10 hour.

Figure 3:
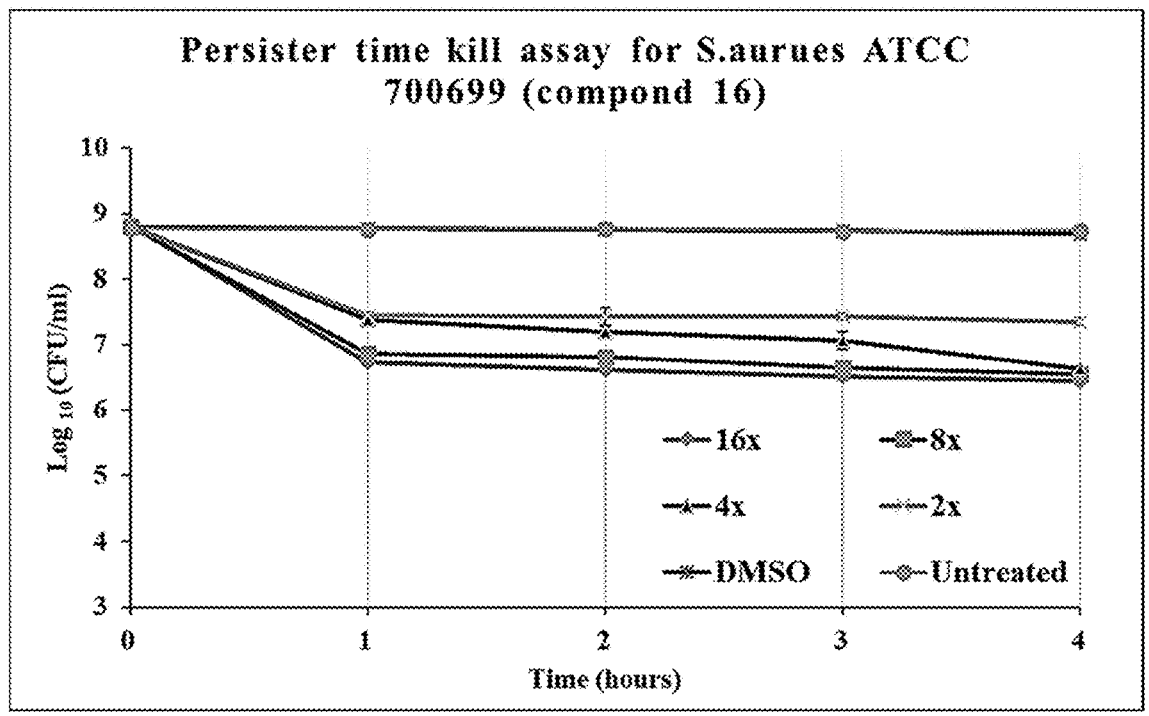
FIG. 3: Activity of the potent compound 16 against the persisters MRSA.
Figure 3:
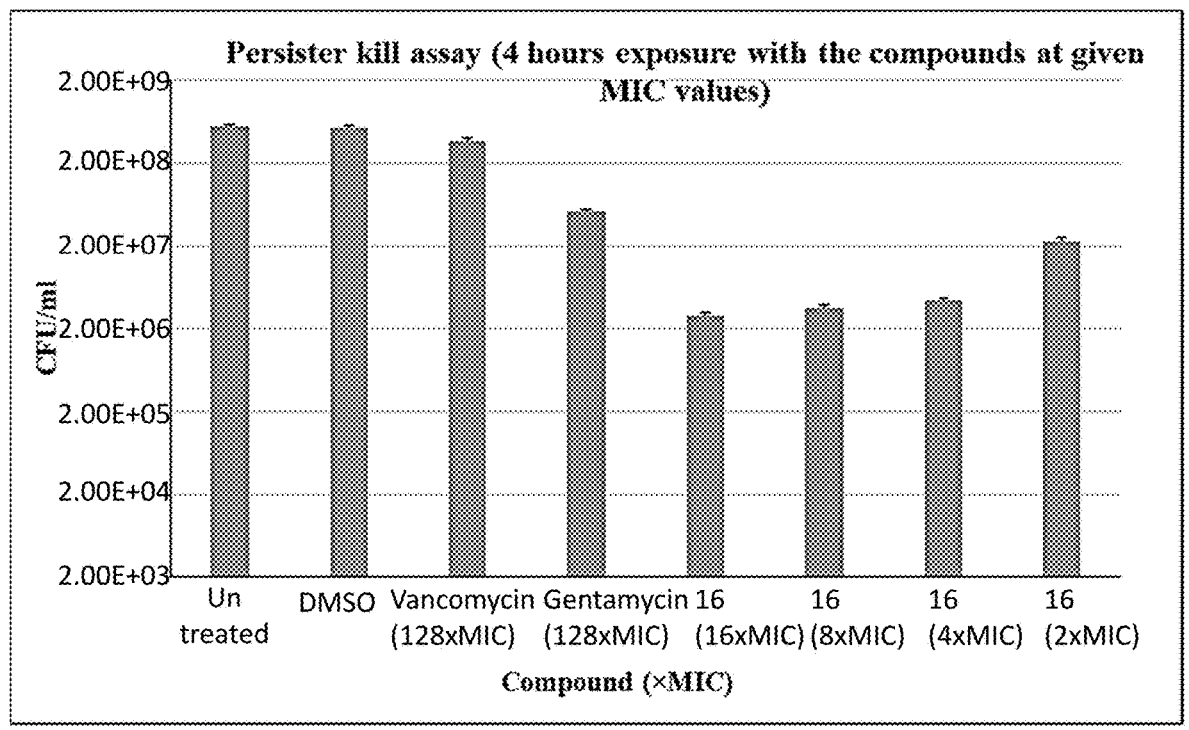
Figure 4:
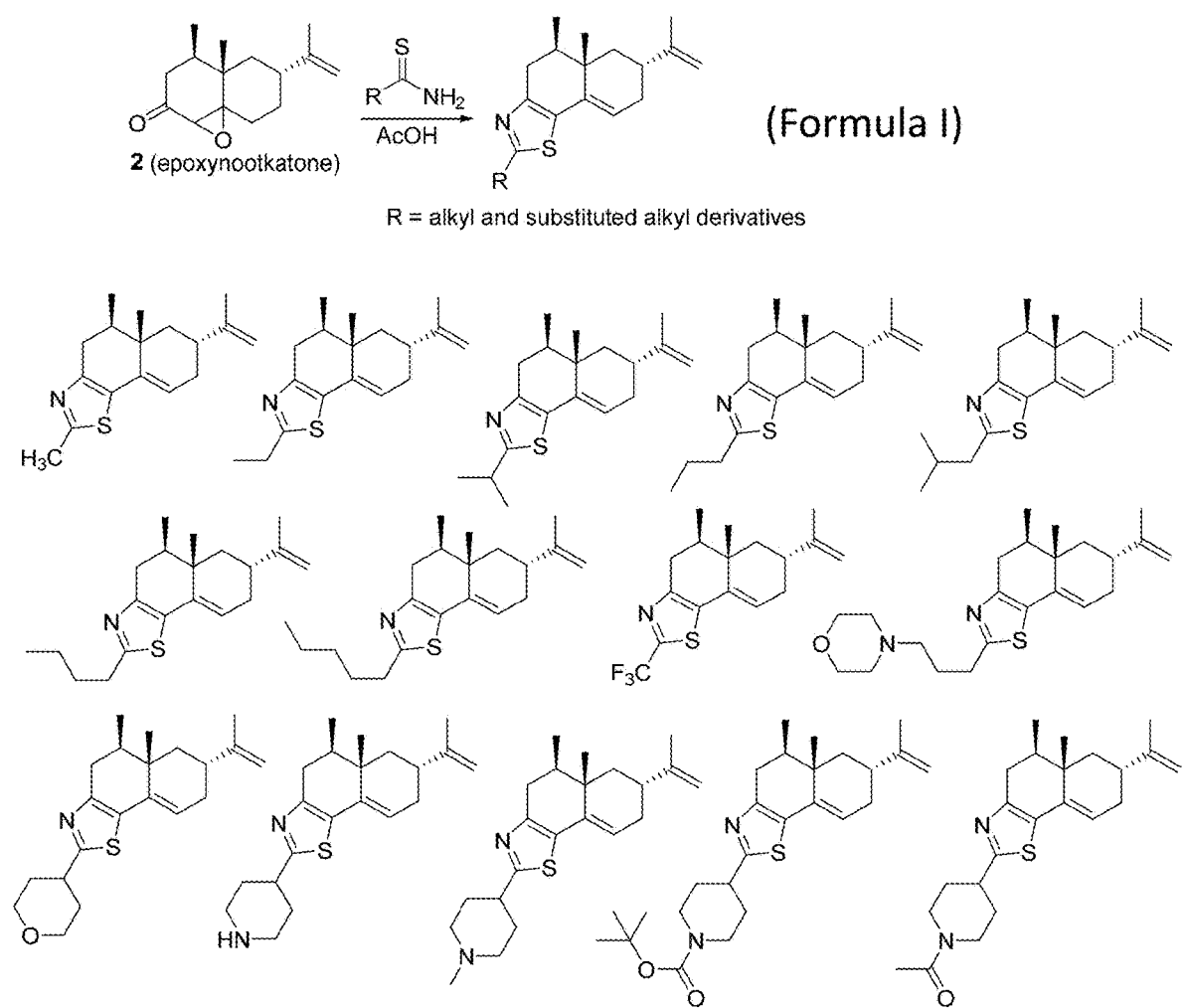
FIG. 4: Scheme and exemplary compounds of Formula I.
Figure 5:
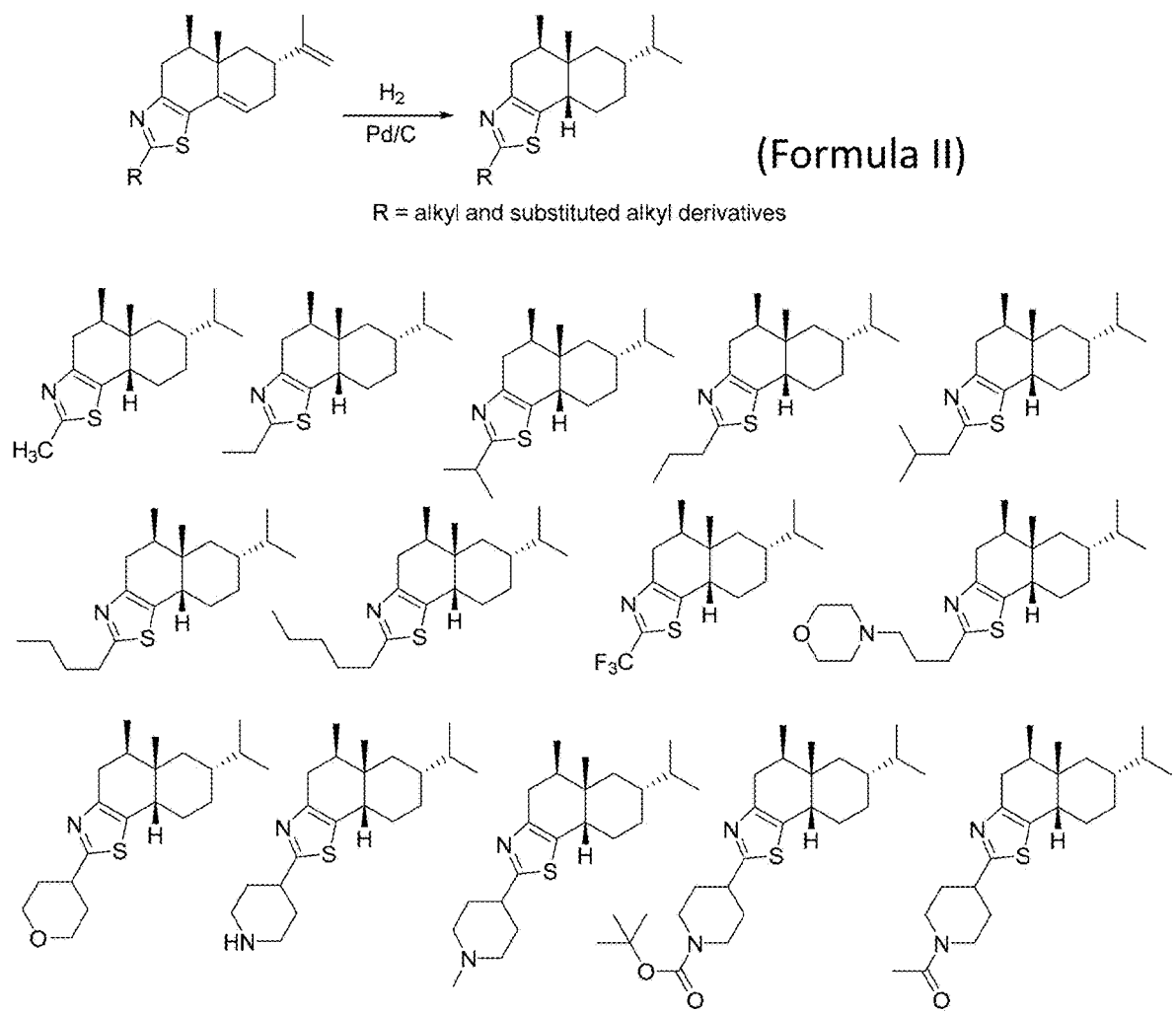
FIG. 5: Scheme and exemplary compounds of Formula II.
Figure 6:
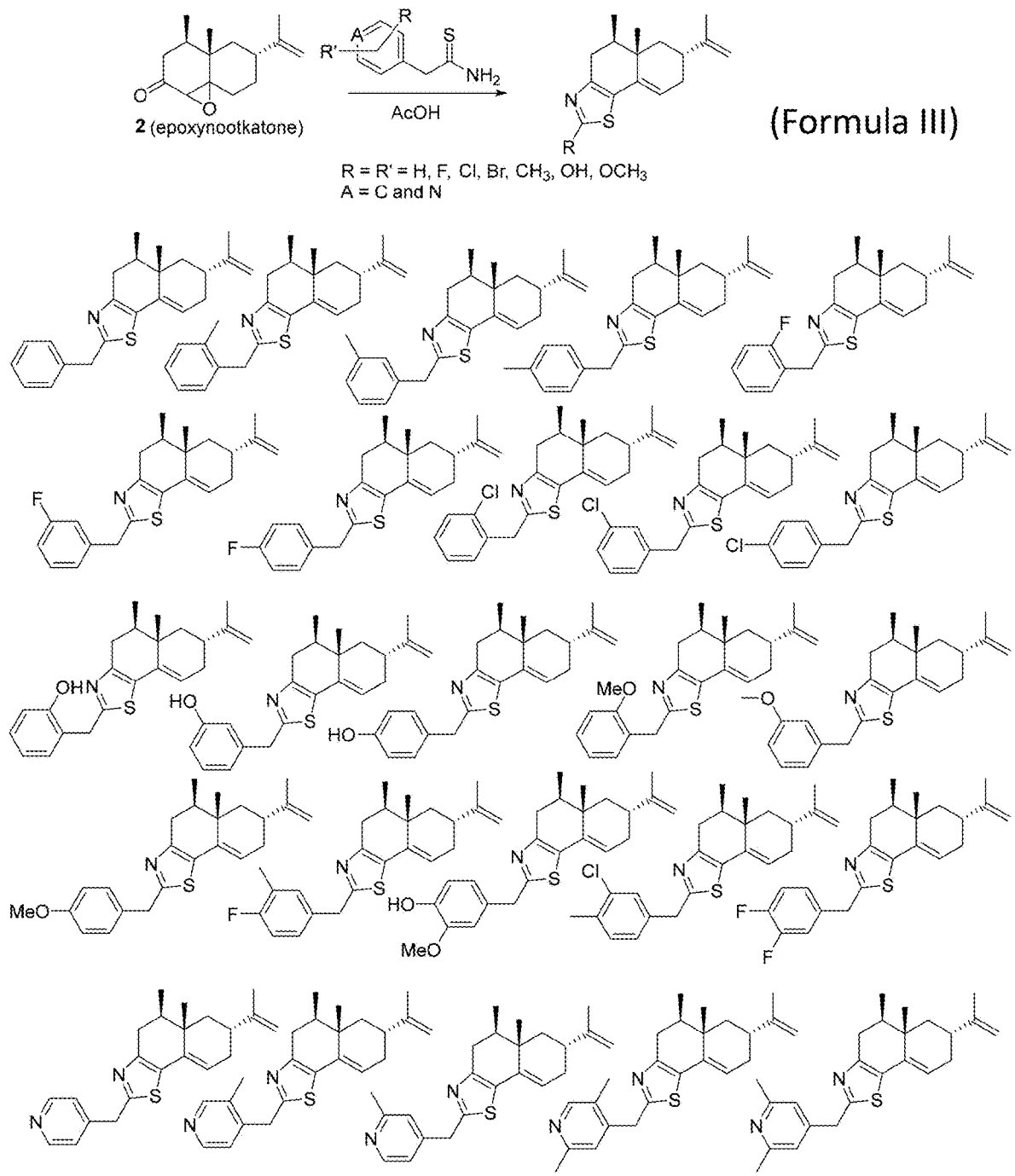
FIG. 6: Scheme and exemplary compounds of Formula III.
Figure 7:
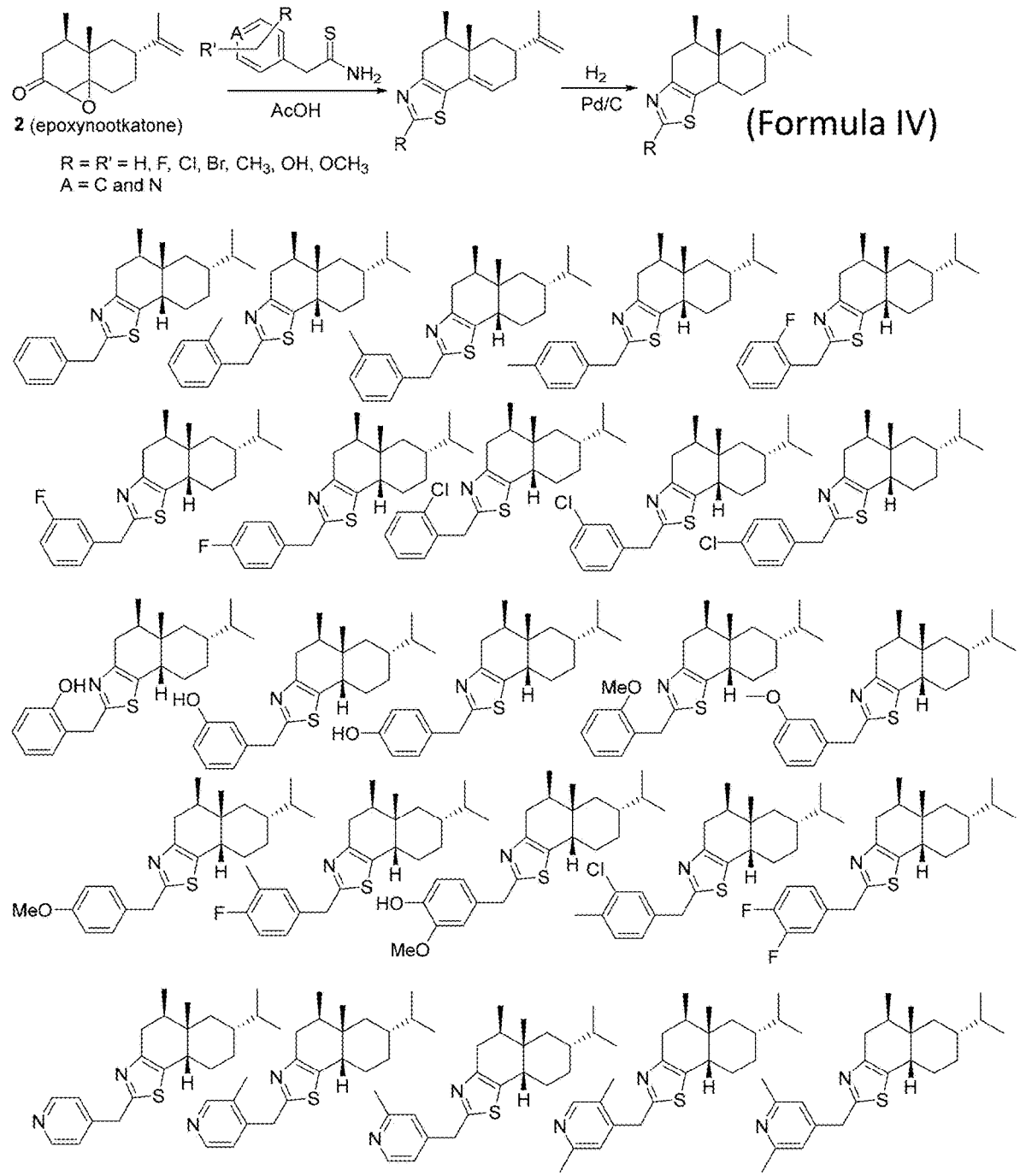
FIG. 7: Scheme and exemplary compounds of Formula IV.
Figure 8:
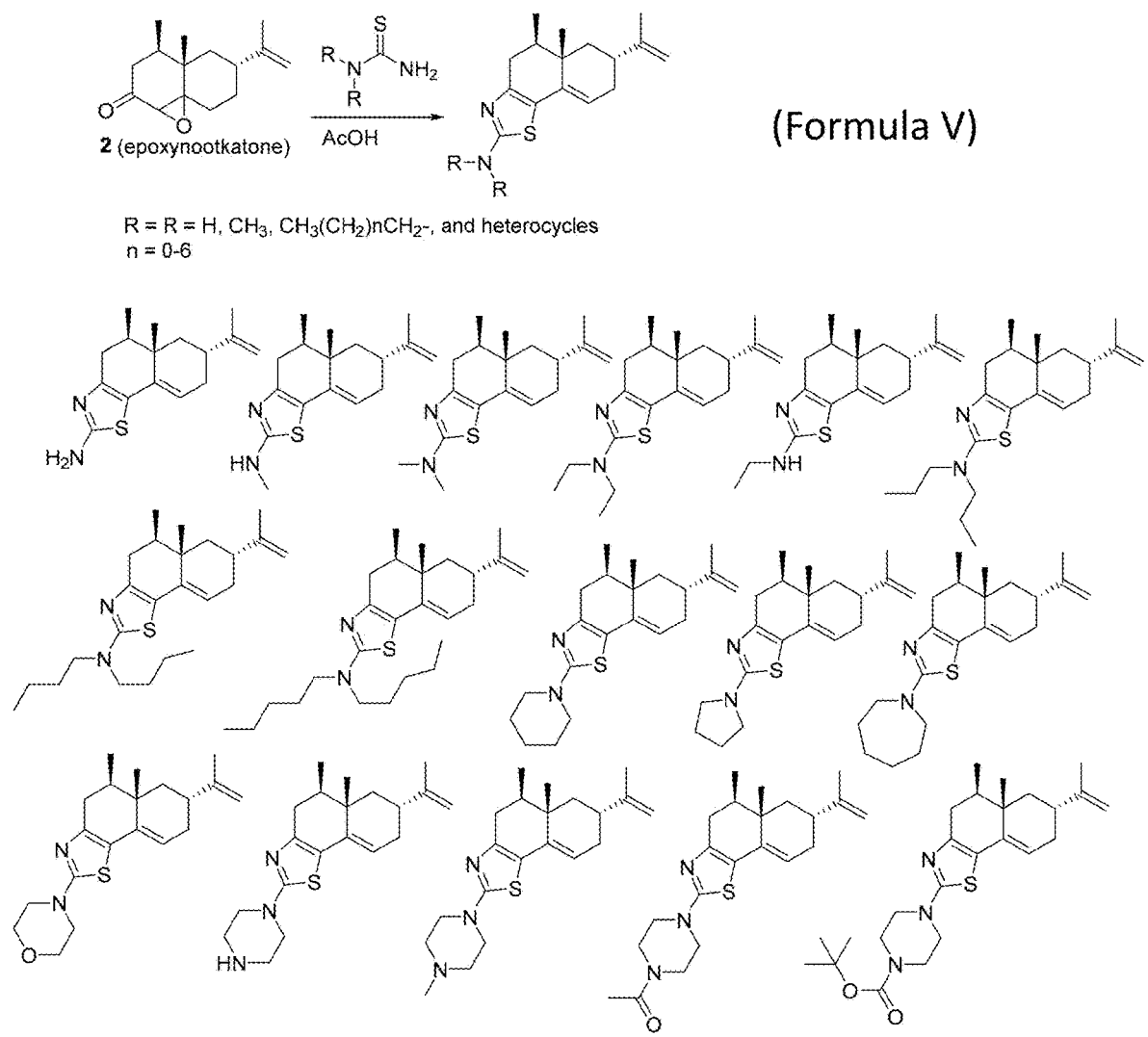
FIG. 8: Scheme and exemplary compounds of Formula V.
Figure 9:
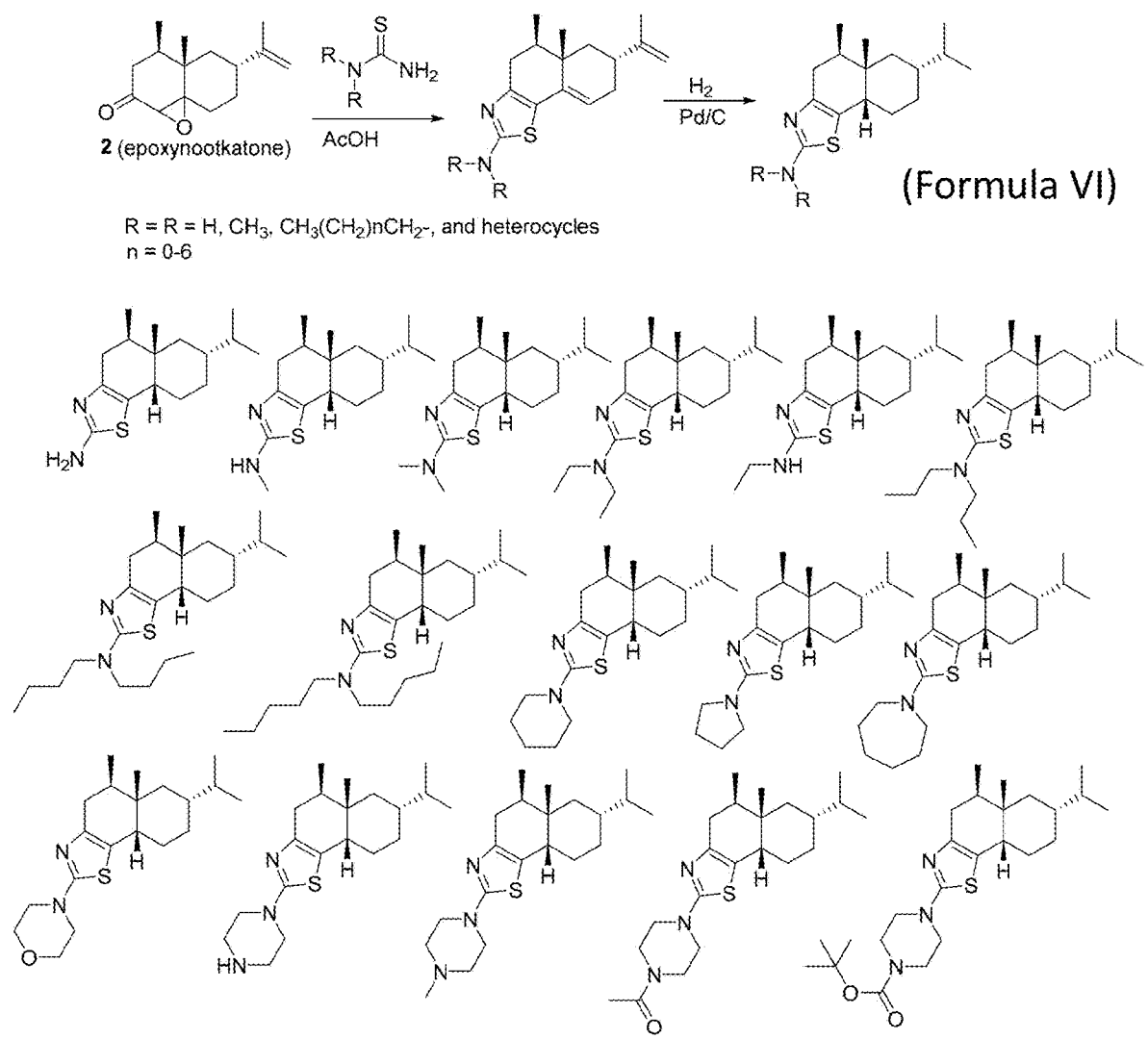
FIG. 9: Scheme and exemplary compounds of Formula VI.
Figure 10:
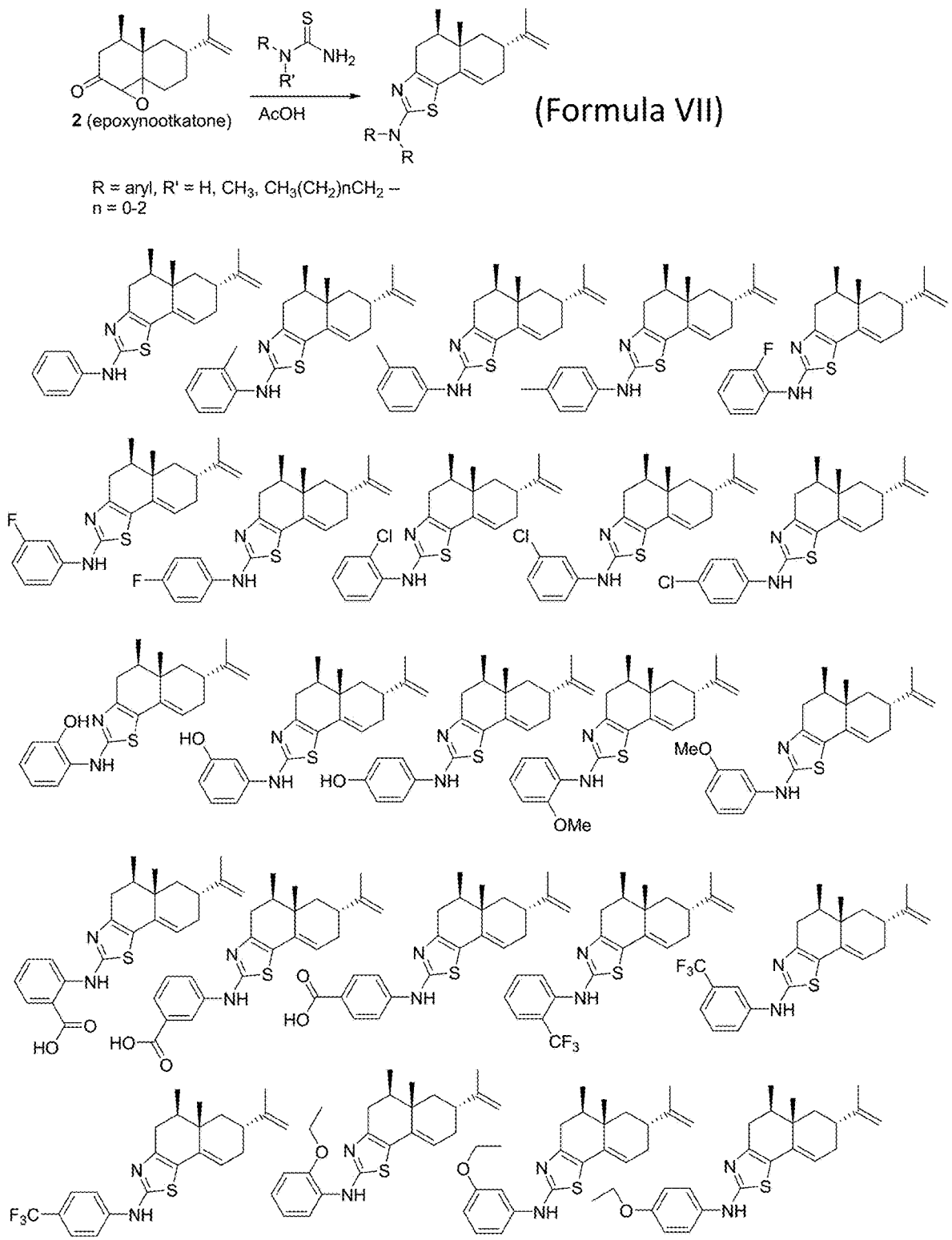
FIG. 10: Scheme and exemplary compounds of Formula VII.
Figure 10:
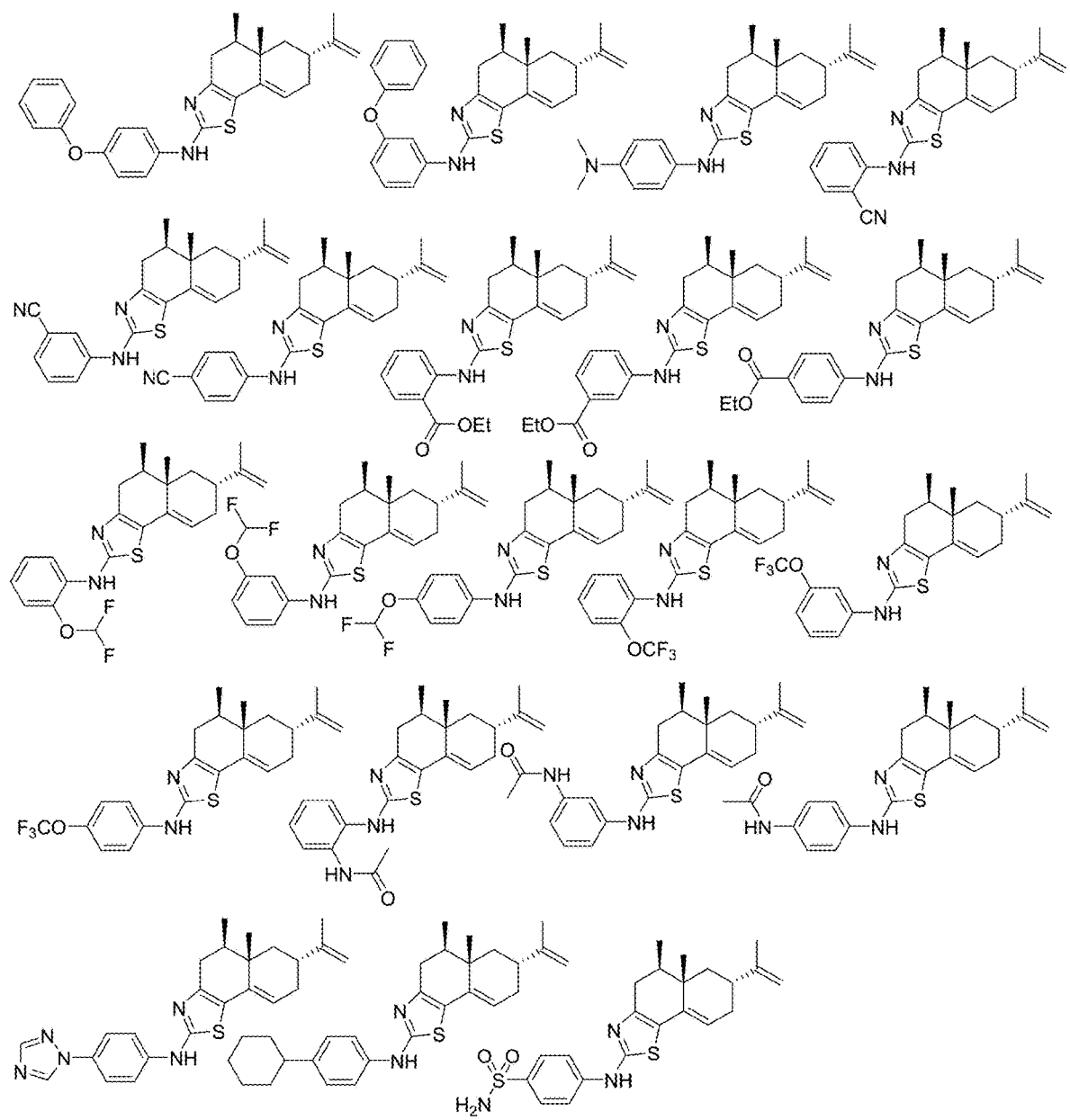
Figure 10:
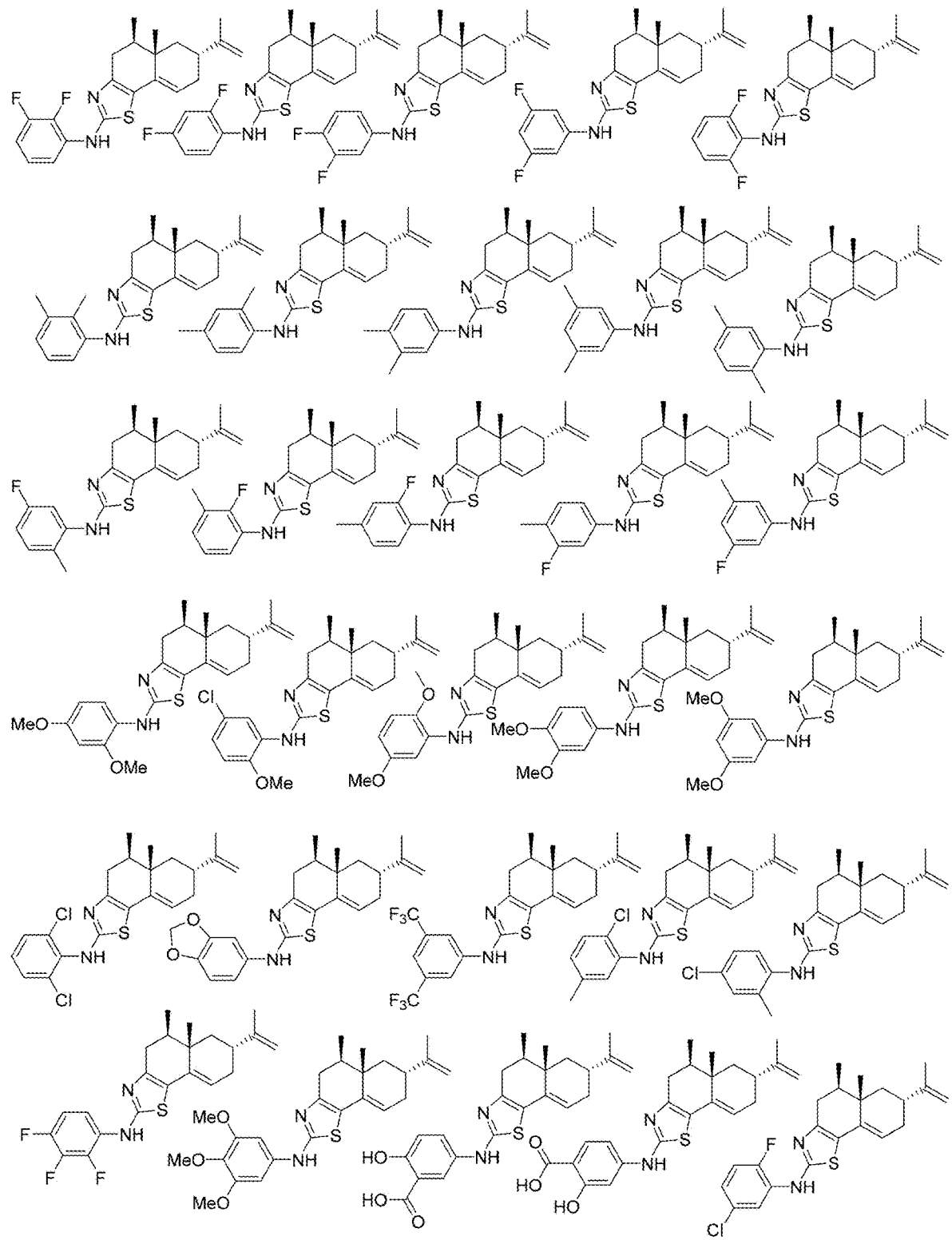
Figure 11:
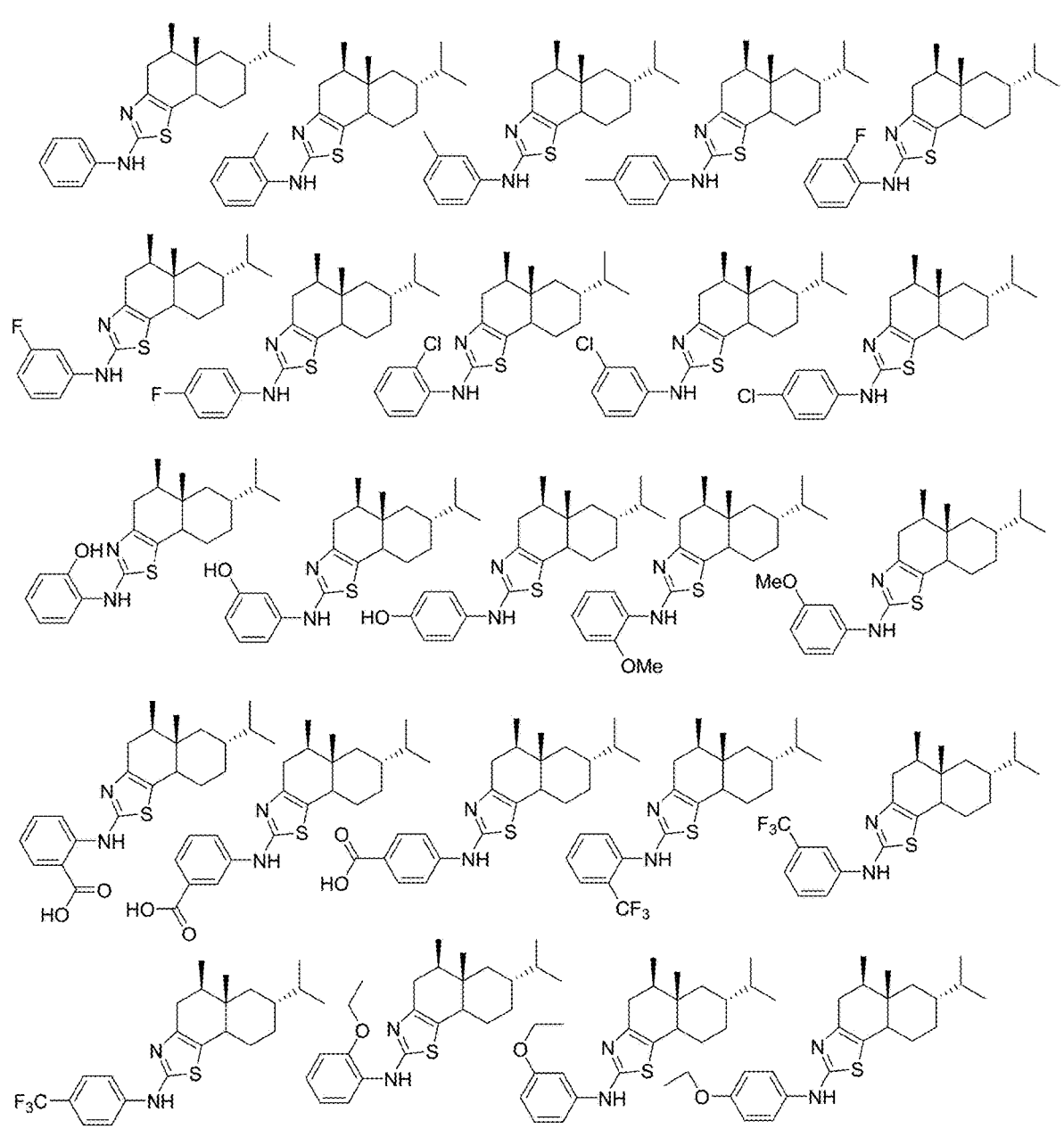
FIG. 11: Scheme and exemplary compounds of Formula VIII.
Figure 11:
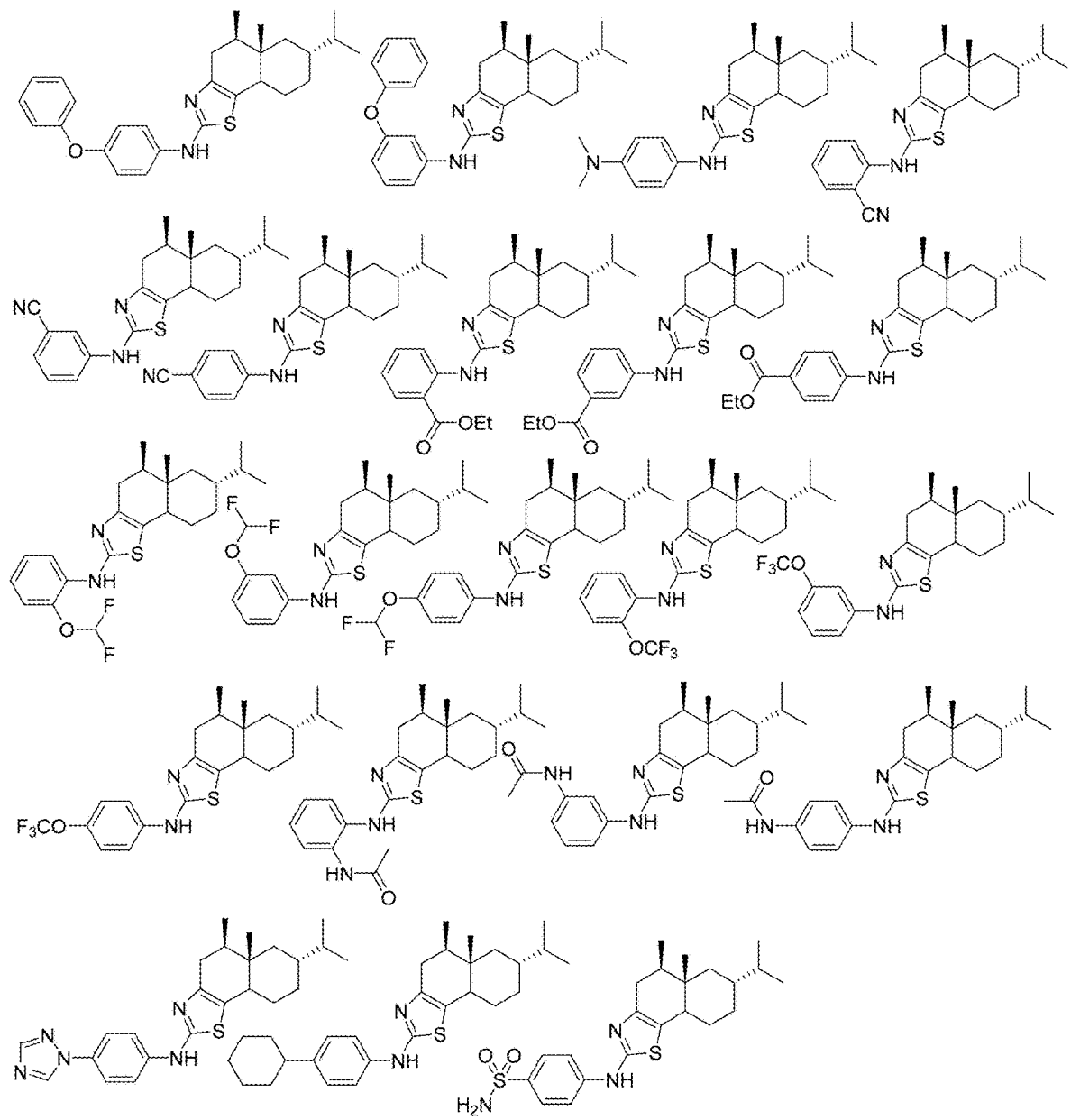
Figure 11:
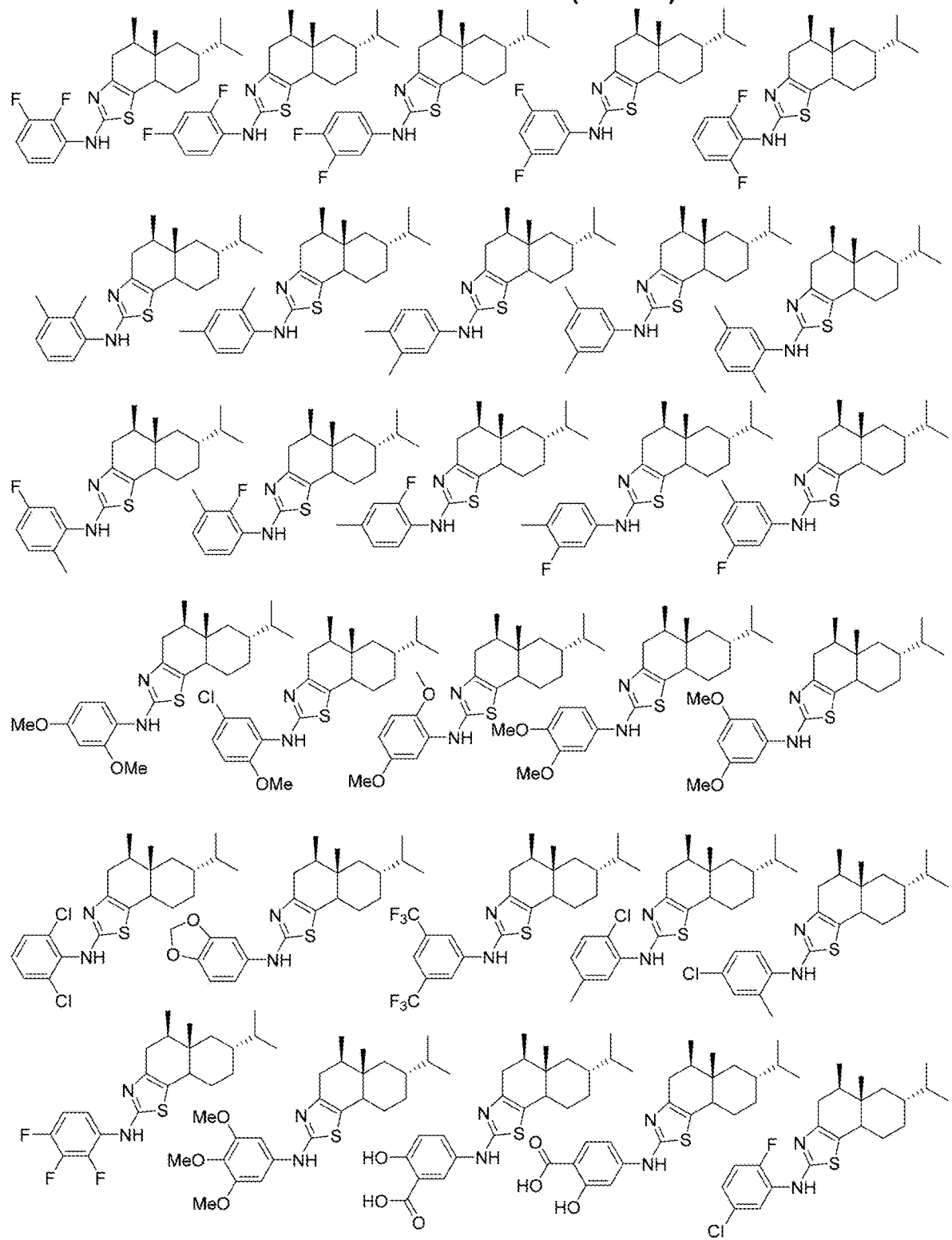

We evaluated the molecule (16) for its ability to kill MRSA persisters and we found that this compound inhibited the growth of persisters significantly (FIG. 3). After 4 hrs exposure of the compound (16) to bacteria, the CFU count was $2 \times 10^7$ and the positive controls vancomycin and gentamycin show $2.4 \times 10^7$ and $2.2 \times 10^8$ count respectively at 128×MIC. With increasing the concentration of the compound (16), CFU count decreased significantly. This compound is several fold more potent than the positive controls (vancomycin and gentamicin) against the persister.

Synthesized compounds (Table 1) were tested against NCI-60 cancer cell lines and found to be non-toxic at 10 μM concentration. See Shoemaker RH. The NCI60 human tumor cell line anticancer drug screen. Nature Rev Cancer 2006; 6: 813-23 for a review of the screen's use. As a result, these compounds may be expected to be non-toxic to healthy cells. An exemplary NCI-60 screen of compound (15) is provided in Table 2.

TABLE 2

| NCI-60 cancer screen | |
|---|---|
| Panel/Cell Line | Growth Percent |
| Leukemia | |
| CCRF-CEM | 99.49 |
| HL-60(TB) | 100.82 |
| K-562 | 92.07 |
| MOLT-4 | 105.32 |
| SR | 113.66 |
| Non-Small Cell Lung Cancer | |
| A549/ATCC | 95.55 |
| EKVX | 101.37 |
| HOP-62 | 95.96 |
| HOP-92 | 96.54 |
| NCI-H226 | 94.10 |
| NCI-H23 | 94.71 |
| NCI-H322M | 102.27 |
| NCI-H460 | 104.69 |
| NCI-H522 | 92.28 |
| Colon Cancer | |
| COLO 205 | 118.41 |
| HCC-2998 | 100.46 |
| HCT-116 | 114.01 |
| HCT-15 | 100.28 |
| HT29 | 105.86 |
| KM12 | 103.49 |
| SW-620 | 103.38 |
| CNS Cancer | |
| SF-268 | 100.98 |
| SF-295 | 92.61 |
| SF-539 | 101.06 |
| SNB-19 | 93.47 |
| SNB-75 | 87.74 |
| U251 | 102.73 |
| Melanoma | |
| LOX IMVI | 101.88 |
| MALME-3M | 99.38 |
| M14 | 98.96 |
| SK-MEL-2 | 104.08 |
| SK-MEL-28 | 106.43 |
| SK-MEL-5 | 99.11 |
| UACC-257 | 100.07 |
| UACC-62 | 93.02 |
| Ovarian Cancer | |
| IGROV1 | 102.22 |
| OVCAR-3 | 102.89 |
| OVCAR-4 | 95.29 |
| OVCAR-5 | 106.63 |
| OVCAR-8 | 98.85 |
| NCI/ADR-RES | 105.66 |
| SK-OV-3 | 109.13 |
| Renal Cancer | |
| 786-0 | 101.31 |
| A498 | 107.24 |
| ACHN | 100.09 |
| CAKI-1 | 99.88 |
| RXF 393 | 113.93 |
| SN12C | 94.92 |
| TK-10 | 118.28 |
| UO-31 | 88.19 |
| Prostate Cancer | |
| PC-3 | 94.38 |
| DU-145 | 104.97 |
| Breast Cancer | |
| MCF7 | 89.98 |
| MDA-MB-231/ATCC | 101.25 |
| HS 578T | 100.94 |
| BT-549 | 115.53 |
| T-47D | 84.40 |
| MDA-MB-468 | 102.12 |
| Mean | 100.94 |
| Delta | 16.54 |
| Range | 34.01 |

These experiments demonstrate that the compounds disclosed herein are antimicrobial agents. Compounds (15) and (16) were determined to be the most potent antimicrobial agent of those tests. Structure activity relationship (SAR) indicated that oxygenated compounds are the most active compounds against the Gram-positive strains. The most potent molecule (16) eliminated *S. aureus* persisters effectively at a low concentration compared to the positive controls.

Minimal inhibitory concentration (MIC) assay The standard microdilution method recommended by the Clinical and Laboratory Standards Institute (CLSI) was used to determine the MIC of the antibiotics. The starting concentration of compounds was 50 μg/ml and 2-fold dilution was done down the 96 honeycomb well plate column. The MIC assay was conducted in triplicates.

Cytotoxicity Against HEK293 Cell Line

Cytotoxicity of the antibiotics was evaluated by using a human embryonic kidney cell line (HEK293). HEK293 cells were grown in Eagle's Minimum Essential Medium (EMEM) with 10% Fetal Bovine Serum (FBS) and incubated at 37° C. in the presence of 5% carbon dioxide. For cytotoxicity assays, HEK293 cells were cultured in 96-well black plates with 4,000 cells per well and treated for 24 hours with a range of concentrations of antibiotics dissolved in DMSO. Resazurin (40 μl of 0.15 mg/ml) was added per well and incubated for additional 4 hours. Reduction of resazurin was measured with excitation at 560 nm and emission at 590 nm using Bio Tek™ Cytation™5 plate reader. $IC_{50}$ values were determined through data processing using Graphpad Prism 7 for Windows, Version 7.04.

Time-Kill Assay

Time kill assay for test antibiotics against *S. aureus* ATCC 700699 and *S. aureus* ATCC 33591 strains was conducted using procedures published previously.[26] Briefly, a log-phase bacterial culture was diluted to $\sim 5 \times 10^6$ CFU/ml in warm sterile CAMHB broth and was exposed to antibiotics at 4×MIC concentration then incubated at 35° C. Samples of 20 μl were taken every 2 hours, diluted 10 fold to $10^{-5}$, and the 6×6 drop plate method was performed to determine viable CFU/ml after 18-24 hours of incubation at 35° C. Each antibiotic time-kill assay was conducted in triplicate.

Persister Cell Killing Assay

A persister cell killing assay was performed following the methodology described by Kim et. al. with some modifications.[28] S. aureus strain was grown to stationary phase in CAMHB medium by shaking at 200 rpm overnight at 35° C. An aliquot of stationary phase culture (1 ml) was washed thrice with 1×PBS by centrifugation. After washing, the cells were diluted to ~5×10$^8$ CFU/ml (confirmed by plate count). Diluted persister cells (2 ml) plus antibiotics at the desired concentration were incubated in sterile 10×75 mm plastic culture tubes at 35° C. with shaking at 200 rpm. At specific times, 400 µl aliquots were placed into microcentrifuge tubes and the cells washed and serially diluted in PBS. The diluted sample was plated on TSA agar plate with 5% sheep blood by the 6×6 drop plate method. Plates were incubated for 18-20 hours at 35° C., and then colonies were counted to calculate concentrations in CFU/ml. The experiment was performed in triplicates.

Example 3. Proteomic Analysis

Quantitative proteomics is widely used in the study of metabolic effects of known antibiotics, synergistic effects of antibiotics, and the mechanisms of drug resistance. The up- and down-regulated proteins of treated bacteria were determined by using quantitative proteomics. Bacteria were treated with a sub-lethal concentration of compound 16, and differentially expressed proteins were compared with the untreated and DMSO treated control groups.

The following literature procedure was used to isolate proteins for quantitative proteomics. [Liu, X. et al., Proteomic response of methicillin-resistant S. aureus to a synergistic antibacterial drug combination: a novel erythromycin derivative and oxacillin. Scientific reports 2016, 6, 19841.] Bacteria were grown in cation-adjusted Muller Hilton Broth treated with ⅛ MIC of compounds. Vancomycin, ciprofloxacin, DMSO (1%), and no treatment were used as controls. Treated flasks were incubated in a shaker at 200 rpm at 35° C. Bacterial cells were harvested at 0.4 OD$_{600}$ by centrifugation resuspended in lysis buffer (8 M urea) and sonicated for 10 min in an ice bath. The lysed mixture was centrifuged at 4000 rpm for 10 min to remove debris and unlysed cells. Proteins were precipitated by adding acetone and storing the supernatant at −20° C. Precipitated proteins were harvested and dissolved in 4M urea and 30 mM Tris-HCl buffer. Protein concentration was measured by Bradford protein assay using bovine serum albumin as standard.

Proteomics assay was performed in an IDeA core facility at the University of Arkansas for Medical Sciences (UAMS), Little Rock. Proteins were reduced, alkylated, and purified by chloroform/methanol extraction prior to digestion with sequencing grade modified porcine trypsin (Promega). Tryptic peptides were separated by reverse phase XSelect CSH C18 2.5 um resin (Waters) on an in-line 150×0.075 mm column using an UltiMate 3000 RSLCnano system (Thermo). Eluted peptides were subjected to mass spectrometry using Orbitrap Exploris 480 mass spectrometer (Thermo). To assemble a chromatogram library, six gas-phase fractions were acquired. Following data acquisition, data were searched using an empirically corrected library and a quantitative analysis was performed to obtain a comprehensive proteomic profile. Proteins were identified and quantified using EncyclopeDIA. [Searle, B. C. et al., Chromatogram libraries improve peptide detection and quantification by data independent acquisition mass spectrometry. Nature Communications 2018, 9, 5128.]

Compound (16) has changed the expression of several proteins as shown in Table 3. As for example, compound (16) has caused the significant change of bacterial ATP-binding cassette (ABC) transporter protein. Docking studies have also shown the strong binding (docking score=−5.6) of our compound with this protein. ABC transporters are important proteins to import nutrients across the bacterial membrane and are potential target for antibacterial drug development.

TABLE 3

Assessment of protein regulation by Compound 16 versus DMSO control

| UniportID | Gene name | Description | Docking score | Log(FC) | Adj. P val. |
|---|---|---|---|---|---|
| | gate | Aspartyl/glutamyl-tRNA (Asn/Gln) amidotransferase subunit C | 2DF4 = −3.463<br>2DQN = −3.570<br>2F2A =<br>2G5H = −5.366<br>2G5I = −6.330 | −2.72248 | 6.03E−06 |
| SAV1617 | | UPF0297 protein SAV1617 | −5.84 | −2.32096 | 6.03E−06 |
| SAV0831 | | Similar to thioredoxin | Q2G000 = 0.57 | −1.29808 | 6.03E−06 |
| SAV1291 | | Thiamine_BP domain-containing protein | −4.16 | −1.39904 | 2.04E−05 |
| | esxA | Type VII secretion system extracellular protein A | | −1.69791 | 4.63E−05 |
| SAV1876 | | Uncharacterized protein | −2.66 | −3.16912 | 6.33E−05 |
| SAV1880 | | UPF0435 protein SAV1880 | | −1.52857 | 0.000258 |
| | rsbV | Anti-sigma-B factor antagonist | −2.53 | −1.19889 | 0.001277 |
| | hit | Hit-like protein involved in cell-cycle regulation | −4.47 | −1.25298 | 0.002636 |
| | acpP | Acyl carrier protein | −3 | −1.46267 | 0.004027 |
| | moaD | Molybdopterin synthase sulfur carrier subunit | | −1.61741 | 0.004027 |
| | ftnA | Bacterial non-heme ferritin | −3.27 | −1.12193 | 0.004027 |
| SAV1615 | | UPF0473 protein SAV1615 | −3.68 | −1.3145 | 0.00524 |
| | narG | Nitrate reductase (quinone) | | −1.5746 | 0.005672 |

TABLE 3-continued

Assessment of protein regulation by Compound 16 versus DMSO control

| UniportID | Gene name | Description | Docking score | Log(FC) | Adj. P val. |
|---|---|---|---|---|---|
| | SAV2592 | 3-dmu-9_3-mt domain-containing protein | −3.18 | −1.10536 | 0.011995 |
| | nasD | Nitrite reductase | −5.56 | −1.20114 | 0.020283 |
| | SAV1556 | ABC transporter MreA | −5.6 | −1.26719 | 0.022183 |
| | SAV0486 | Initiation-control protein YabA | −1.37 | −1.07618 | 0.044334 |
| A0A0H3-JPA5 | mecA | Penicillin binding protein 2 prime | 3ZFZ = −4.413 | 1.377979 | 0.000173 |
| A0A0H3-JUX1 | SAV1155 | Fibrinogen-binding protein | −5.003 | 4.340739 | 0.000705 |
| A0A0H3-JQ49 | SAV0307 | Similar to outer membrane protein | −5.747 | 1.312765 | 0.00524 |
| Q931F4 | sbi | Immuno-globulin-binding protein Sbi | −6.461 | 1.710144 | 0.00524 |
| A0A0H3-JPA2 | coa | Staphyl-ocoagulase | −5.859 | 4.523752 | 0.010992 |
| P65288 | lip1 | Lipase 1 | −6.615 | 1.631022 | 0.026932 |

REFERENCES

1. Harvey, A. L.; Edrada-Ebel, R.; Quinn, R. J., The re-emergence of natural products for drug discovery in the genomics era. *Nature Reviews Drug Discovery* 2015, 14 (2), 111-129.
2. Sauer, A. M.; Fronczek, F. R.; Zhu, B. C. R.; Crowe, W. E.; Henderson, G.; Laine, R. A., The sesquiterpenoid nootkatone and the absolute configuration of a dibromo derivative. *Acta Crystallogr C* 2003, 59 (Pt 5), o254-6.
3. FDA Nootkatone Now Registered by EPA. https://www.epa.gov/pesticides/nootkatone-now-registered-epa (accessed 10/30/2020).
4. Seo, E. J.; Lee, D.-U.; Kwak, J. H.; Lee, S.-M.; Kim, Y. S.; Jung, Y.-S., Antiplatelet effects of *Cyperus rotundus* and its component (+)-nootkatone. *Journal of Ethnopharmacology* 2011, 135 (1), 48-54.
5. Murase, T.; Misawa, K.; Haramizu, S.; Minegishi, Y.; Hase, T., Nootkatone, a characteristic constituent of grapefruit, stimulates energy metabolism and prevents diet-induced obesity by activating AMPK. *American journal of physiology. Endocrinology and metabolism* 2010, 299 (2), E266-75.
6. He, B.; Xu, F.; Xiao, F.; Yan, T.; Wu, B.; Bi, K.; Jia, Y., Neuroprotective effects of nootkatone from *Alpiniae oxyphyllae* Fructus against amyloid-β-induced cognitive impairment. *Metabolic Brain Disease* 2018, 33 (1), 251-259.
7. Duplan, V.; Serba, C.; Garcia, J.; Valot, G.; Barluenga, S.; Hoerle, M.; Cuendet, M.; Winssinger, N., Synthesis of sesquiterpene-inspired derivatives designed for covalent binding and their inhibition of the NF-κB pathway. *Org. Biomol. Chem.* 2014, 12 (2), 370-375.
8. Guo, Y.; Liu, Z.; Hou, E.; Ma, N.; Fan, J.; Jin, C.-Y.; Yang, R., Non-food bioactive natural forest products as insecticide candidates: Preparation, biological evaluation and molecular docking studies of novel N-(1,3-thiazol-2-yl) carboxamides fused (+)-nootkatone from *Chamaecyparis nootkatensis* [D. Don] Spach. *Industrial Crops and Products* 2020, 156, 112864.
9. Wang, Y.; Liu, Q.; Wei, Z.; Liu, N.; Li, Y.; Li, D.; Jin, Z.; Xu, X., Thiazole Amides, A Novel Class of Algaecides against Freshwater Harmful Algae. *Scientific reports* 2018, 8 (1), 8555.
10. Palomo, S.; González, I.; De la Cruz, M.; Martin, J.; Tormo, J. R.; Anderson, M.; Hill, R. T.; Vicente, F.; Reyes, F.; Genilloud, O., Sponge-Derived *Kocuria* and *Micrococcus* spp. as Sources of the New Thiazolyl Peptide Antibiotic Kocurin. *Mar Drugs* 2013, 11 (4), 1071-1086.
11. Ayati, A.; Emami, S.; Asadipour, A.; Shafiee, A.; Foroumadi, A., Recent applications of 1,3-thiazole core structure in the identification of new lead compounds and drug discovery. *European Journal of Medicinal Chemistry* 2015, 97, 699-718.
12. CDC About Antibiotic Resistance. https://www.cdc.gov/drugresistance/about.html (accessed 10/30/2020).
13. CDC Methicillin-resistant *Staphylococcus aureus* (MRSA). https://www.cdc.gov/mrsa/index.html (accessed 10/30/2020).
14. Brider, J.; Rowe, T.; Gibler, D. J.; Gottsponer, A.; Delancey, E.; Branscum, M. D.; Ontko, A.; Gilmore, D.; Alam, M. A., Synthesis and antimicrobial studies of azomethine and N-arylamine derivatives of 4-(4-formyl-3-phenyl-1H-pyrazol-1-yl)benzoic acid as potent anti-methicillin-resistant *Staphylococcus aureus* agents. *Med. Chem. Res.* 2016, 25 (11), 2691-2697.
15. Whitt, J.; Duke, C.; Sumlin, A.; Chambers, S. A.; Alnufaie, R.; Gilmore, D.; Fite, T.; Basnakian, A. G.; Alam, M. A., Synthesis of Hydrazone Derivatives of 4-[4-Formyl-3-(2-oxochromen-3-yl)pyrazol-1-yl]benzoic acid as Potent Growth Inhibitors of Antibiotic-resistant *Staphylococcus aureus* and *Acinetobacter baumannii*. *Molecules* 2019, 24 (11), 2051.
16. Alnufaie, R.; Raj KC, H.; Alsup, N.; Whitt, J.; Andrew Chambers, S.; Gilmore, D.; Alam, M. A., Synthesis and Antimicrobial Studies of Coumarin-Substituted Pyrazole Derivatives as Potent Anti-*Staphylococcus aureus* Agents. *Molecules* 2020, 25 (12), 2758.
17. Alnufaie, R.; Alsup, N.; Kc, H. R.; Newman, M.; Whitt, J.; Chambers, S. A.; Gilmore, D.; Alam, M. A., Design and synthesis of 4-[4-formyl-3-(2-naphthyl)pyrazol-1-yl] benzoic acid derivatives as potent growth inhibitors of drug-resistant *Staphylococcus aureus*. *The Journal of Antibiotics* 2020.
18. Ali, M. A.; Okolo, C.; Alsharif, Z. A.; Whitt, J.; Chambers, S. A.; Varma, R. S.; Alam, M. A., Benign Synthesis of Thiazolo-androstenone Derivatives as Potent Anticancer Agents. *Org. Lett.* 2018, 20 (18), 5927-5932.
19. Okolo, C.; Ali, M. A.; Newman, M.; Chambers, S. A.; Whitt, J.; Alsharif, Z. A.; Day, V. W.; Alam, M. A., Hexafluoroisopropanol-Mediated Domino Reaction for the Synthesis of Thiazolo-androstenones: Potent Anticancer Agents. *ACS Omega* 2018, 3 (12), 17991-18001.
20. Sauer, A. M.; Crowe, W. E.; Henderson, G.; Laine, R. A., An Efficient and Economic Asymmetric Synthesis of (+)-Nootkatone, Tetrahydronootkatone, and Derivatives. *Org. Lett.* 2009, 11 (16), 3530-3533.

21. Handore, K. L.; Seetharamsingh, B.; Reddy, D. S., Ready Access to Functionally Embellished cis-Hydrindanes and cis-Decalins: Protecting Group-Free Total Syntheses of (±)-Nootkatone and (±)-Noreremophilane. *The Journal of Organic Chemistry* 2013, 78 (16), 8149-8154.
22. Majetich, G.; Behnke, M.; Hull, K., A stereoselective synthesis of (.+−.)-nootkatone and (.+−.)-valencene via an intramolecular Sakurai reaction. *The Journal of Organic Chemistry* 1985, 50 (19), 3615-3618.
23. Pesaro, M.; Bozzato, G.; Schudel, P., The total synthesis of racemic nootkatone. *Chemical Communications (London)* 1968, (19), 1152-1154.
24. Alsharif, Z. A.; Alam, M. A., Modular synthesis of thiazoline and thiazole derivatives by using a cascade protocol. *RSC Advances* 2017, 7 (52), 32647-32651.
25. Whitt, J.; Duke, C.; Ali, M. A.; Chambers, S. A.; Khan, M. M. K.; Gilmore, D.; Alam, M. A., Synthesis and Antimicrobial Studies of 4-[3-(3-Fluorophenyl)-4-formyl-1H-pyrazol-1-yl]benzoic Acid and 4-[3-(4-Fluorophenyl)-4-formyl-1H-pyrazol-1-yl]benzoic Acid as Potent Growth Inhibitors of Drug-Resistant Bacteria. *ACS Omega* 2019, 4 (10), 14284-14293.
26. Alnufaie, R.; Alsup, N.; Kc, H. R.; Newman, M.; Whitt, J.; Chambers, S. A.; Gilmore, D.; Alam, M. A., Design and synthesis of 4-[4-formyl-3-(2-naphthyl)pyrazol-1-yl] benzoic acid derivatives as potent growth inhibitors of drug-resistant *Staphylococcus aureus*. *The Journal of Antibiotics* 2020, 73 (12), 818-827.
27. Alarcón-Manjarrez, C.; Arcos-Ramos, R.; Álamo, M. F.; Iglesias-Arteaga, M. A., Synthesis, NMR and crystal characterization of dimeric terephthalates derived from epimeric 4,5-seco-cholest-3-yn-5-ols. *Steroids* 2016, 109, 66-72.
28. Kim, W.; Steele, A. D.; Zhu, W.; Csatary, E. E.; Fricke, N.; Dekarske, M. M.; Jayamani, E.; Pan, W.; Kwon, B.; Sinitsa, I. F.; Rosen, J. L.; Conery, A. L.; Fuchs, B. B.; Vlahovska, P. M.; Ausubel, F. M.; Gao, H.; Wuest, W. M.; Mylonakis, E., Discovery and Optimization of nTZDpa as an Antibiotic Effective Against Bacterial Persisters. *ACS Infectious Diseases* 2018, 4 (11), 1540-1545.

What is claimed:

1. A compound of formula

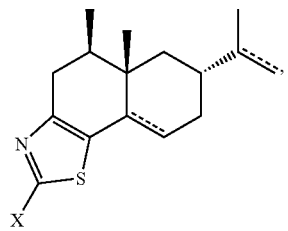

or a pharmaceutically acceptable salt thereof, wherein ≡≡≡ represents a saturated or an unsaturated bond and X is selected from a substituted or an unsubstituted aryl, a substituted or an unsubstituted alkyl, a substituted or an unsubstituted heterocycle, —NR$^1$R$^2$ wherein R$^1$ and R$^2$ are independently selected from hydrogen, a substituted or an unsubstituted aryl, a substituted or an unsubstituted alkyl, or R$^1$ and R$^2$ together form a substituted or an unsubstituted heterocycle;

wherein the heterocycle is a saturated, partially unsaturated, or aromatic 3- to 10-membered ring structure whose ring structure includes one to four heteroatoms selected from S, N, and O;

wherein the substituted aryl has one or more substituents selected from hydroxyl, a halo-substituted or unsubstituted alkyl, a halo-substituted or unsubstituted alkoxyl, halo, nitro, and any combination thereof, the substituted aryl is substituted at two positions with —OR'O— forming a bicyclic group with the aryl and where R' is alkylene, or the substituted aryl has one or more —O-heterocycle and the heterocycle is substituted or unsubstituted;

wherein the substituted alkyl has one or more substituents selected from aryl, substituted aryl, halo, and any combination thereof, and wherein the substituted heterocycle has a substitution selected from one or more substituents selected from alkyl, substituted alkyl, —C(O)OR" substituents and R" is selected from hydrogen or alkyl, and any combination thereof.

2. The compound of claim 1, wherein ≡≡≡ is the unsaturated bond.

3. The compound of claim 1, wherein ≡≡≡ is the saturated bond.

4. The compound of claim 1, wherein X is the substituted or the unsubstituted aryl.

5. The compound of claim 1, wherein X is the substituted or the unsubstituted alkyl.

6. The compound of claim 1, wherein X is the substituted or the unsubstituted heterocycle.

7. The compound of claim 1, wherein X is —NR$^1$R$^2$.

8. The compound of claim 1, wherein ≡≡≡ is an unsaturated bond and X is selected from

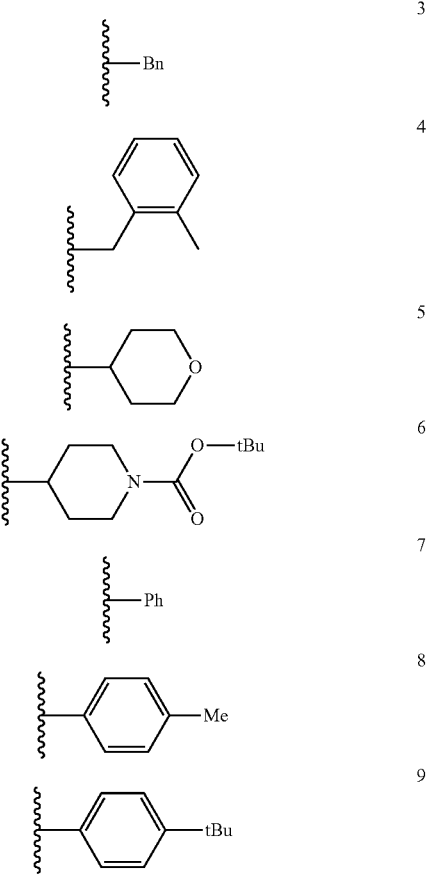

-continued
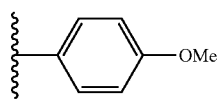  10
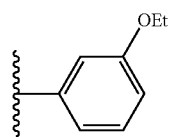  11
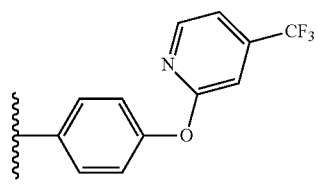  12
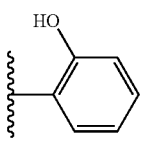  13
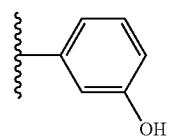  14
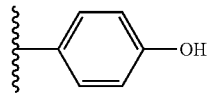  15
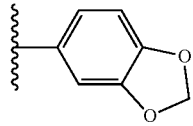  16
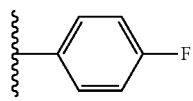  17
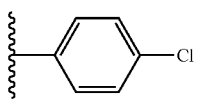  18
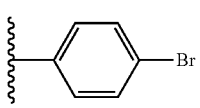  19
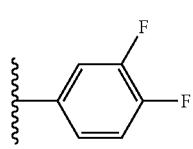  20
21
-continued
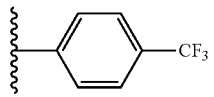  22
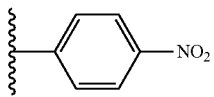  23
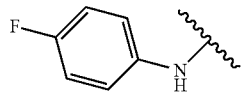  24
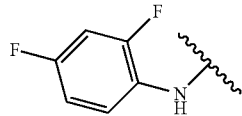  25
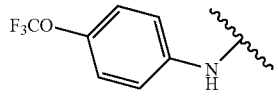  26
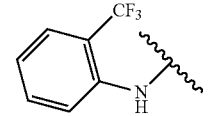  27
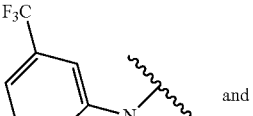  28
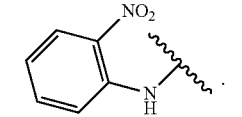  29
9. The compound of claim 8, wherein X is
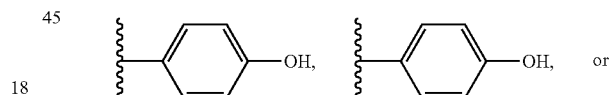
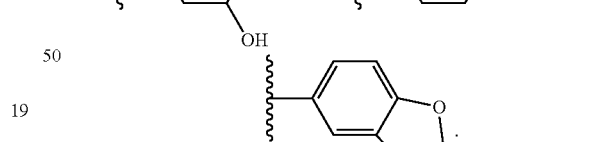
10. The compound of claim 8, wherein X is
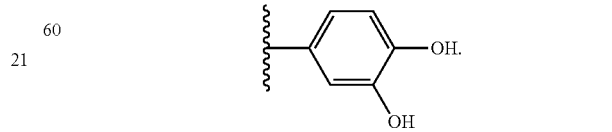
11. A pharmaceutical composition comprising an effective amount of the compound according to claim 1 and a pharmaceutically acceptable excipient, carrier, or diluent.

12. A method for the treatment of a subject in need of a treatment for an infection by a microbe, the method comprising administering an effective amount of the compound according to claim 1 or a pharmaceutical composition comprising the effective amount of the compound to the subject, wherein the microbe is a bacterium.

13. The method of claim 12, wherein the microbe is antimicrobial resistant.

14. The method of claim 12, wherein the microbe is the persister.

15. The method of claim 12, wherein the microbe is a Gram-positive bacterium.

16. The method of claim 15, wherein the Gram-positive bacterium is *S. aureus*, a *S. epidermidis*, *B. subtilis*, or *E. faecium*.

17. The method of claim 15, wherein the Gram-positive bacterium is a methicillin-resistant *S. aureus*.

18. The method of claim 12, wherein the microbe is a Gram-negative bacterium.

19. The method of claim 18, wherein the Gram-negative bacterium is *A. baumannii*.

20. A method for inhibiting growth or proliferation or killing a microbe, the method comprising contacting the microbe with an effective amount of the compound according to claim 1, wherein the microbe is a bacterium.

\* \* \* \* \*